United States Patent
Peplow et al.

(10) Patent No.: US 12,276,636 B2
(45) Date of Patent: Apr. 15, 2025

(54) SURFACE ISOLATION RESISTANCE COMPATIBILITY TEST SYSTEM AND METHOD

(71) Applicant: Tannas Company, Midland, MI (US)

(72) Inventors: Mitchell Andrew Peplow, Darley Dale (GB); Gregory James Hunt, Derby (GB); Christopher Paul Prengaman, Willoughby Hills, OH (US); Rahmeen Fatima Javaid, Milton Keynes (GB)

(73) Assignee: Tannas Company, Midland, MI (US)

( * ) Notice: Subject to any disclaimer, the term of this patent is extended or adjusted under 35 U.S.C. 154(b) by 126 days.

(21) Appl. No.: 17/925,965

(22) PCT Filed: May 28, 2021

(86) PCT No.: PCT/US2021/034957
§ 371 (c)(1),
(2) Date: Nov. 17, 2022

(87) PCT Pub. No.: WO2021/247428
PCT Pub. Date: Dec. 9, 2021

(65) Prior Publication Data
US 2023/0194475 A1 Jun. 22, 2023

Related U.S. Application Data

(60) Provisional application No. 63/032,893, filed on Jun. 1, 2020.

(51) Int. Cl.
*G01N 27/74* (2006.01)
*G01N 33/28* (2006.01)

(52) U.S. Cl.
CPC ......... *G01N 27/74* (2013.01); *G01N 33/2888* (2013.01)

(58) Field of Classification Search
CPC ..... G01N 27/74; G01N 27/07; G01N 33/2888
See application file for complete search history.

(56) References Cited

U.S. PATENT DOCUMENTS

| | | | |
|---|---|---|---|
| 7,285,516 B2 | 10/2007 | Carrick et al. | |
| 2004/0060344 A1* | 4/2004 | Kauffman | G01N 33/2888 73/53.01 |

(Continued)

FOREIGN PATENT DOCUMENTS

| | | | | |
|---|---|---|---|---|
| GB | 1558507 A | * | 1/1980 | F01M 11/10 |
| WO | WO2000079256 A1 | | 12/2000 | |

*Primary Examiner* — Lee E Rodak
*Assistant Examiner* — Demetrius R Pretlow
(74) *Attorney, Agent, or Firm* — Fay Sharpe/Lippes Mathias; Christopher John Rudy

(57) ABSTRACT

A system for detecting deposit formation on electrically-conductive materials in liquid and vapor phases includes a test cell for receiving a test liquid, for example. a lubricant, A heater heats the test liquid to generate a vapor phase of the test liquid in the test cell. A support frame supports at least a first set of electrical conductors in the test liquid, liquid phase, and at least a second set of electrical conductors in the vapor phase, each including a live and a neutral electrical conductor. A power source supplies electric current to the live electrical conductors. A sensor detects an electrical property in each set of conductors, which changes in response to formation of an electrically-conductive deposit connecting the first and second conductors in a respective set of conductors. Preferably, the electrical properties are detected by magnetic sensors such as Hall effect or eddy current sensors.

21 Claims, 15 Drawing Sheets

(56) References Cited

U.S. PATENT DOCUMENTS

| | | | |
|---|---|---|---|
| 2006/0105467 A1* | 5/2006 | Niksa | G01N 27/126 436/150 |
| 2010/0197536 A1 | 8/2010 | Mosier et al. | |
| 2015/0038385 A1 | 2/2015 | Barton et al. | |
| 2017/0247628 A1 | 8/2017 | Cook et al. | |
| 2017/0269036 A1* | 9/2017 | Foord | G01N 27/023 |
| 2018/0364141 A1* | 12/2018 | Youssef | G01V 3/08 |
| 2019/0177649 A1 | 6/2019 | Hong et al. | |
| 2019/0249102 A1 | 8/2019 | Martin et al. | |
| 2019/0367833 A1 | 12/2019 | Hanthorn et al. | |
| 2020/0123463 A1 | 4/2020 | Mosier et al. | |
| 2020/0286811 A1* | 9/2020 | Komo | H01L 23/40 |
| 2021/0214152 A1* | 7/2021 | Thompson | B65D 1/40 |

* cited by examiner

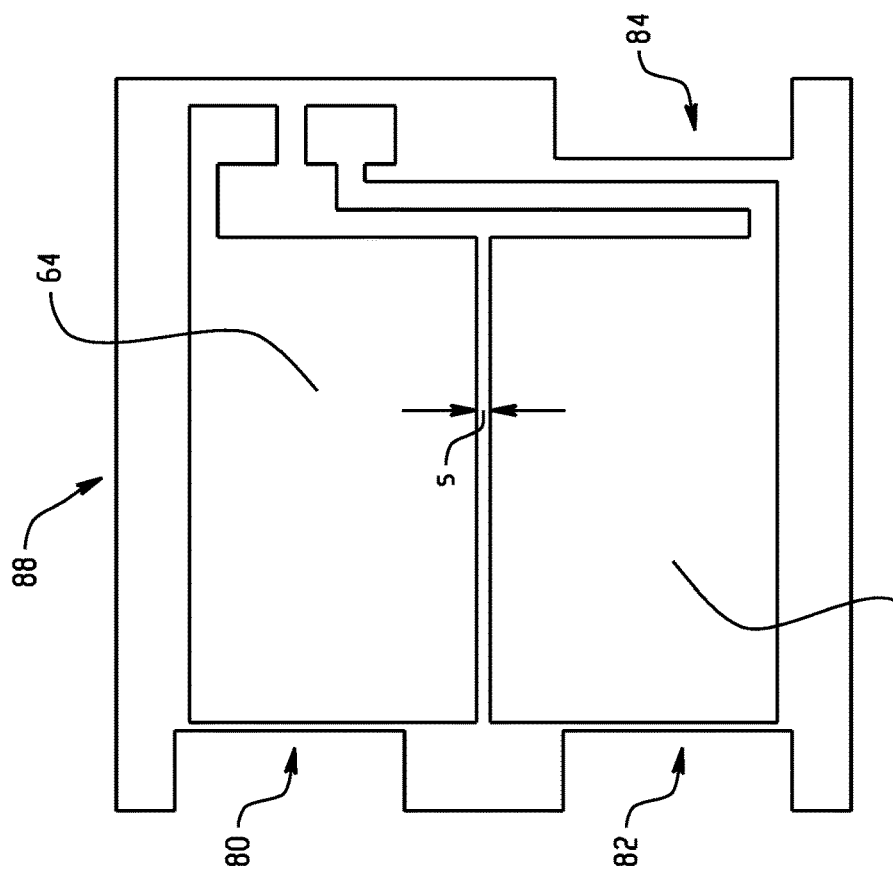
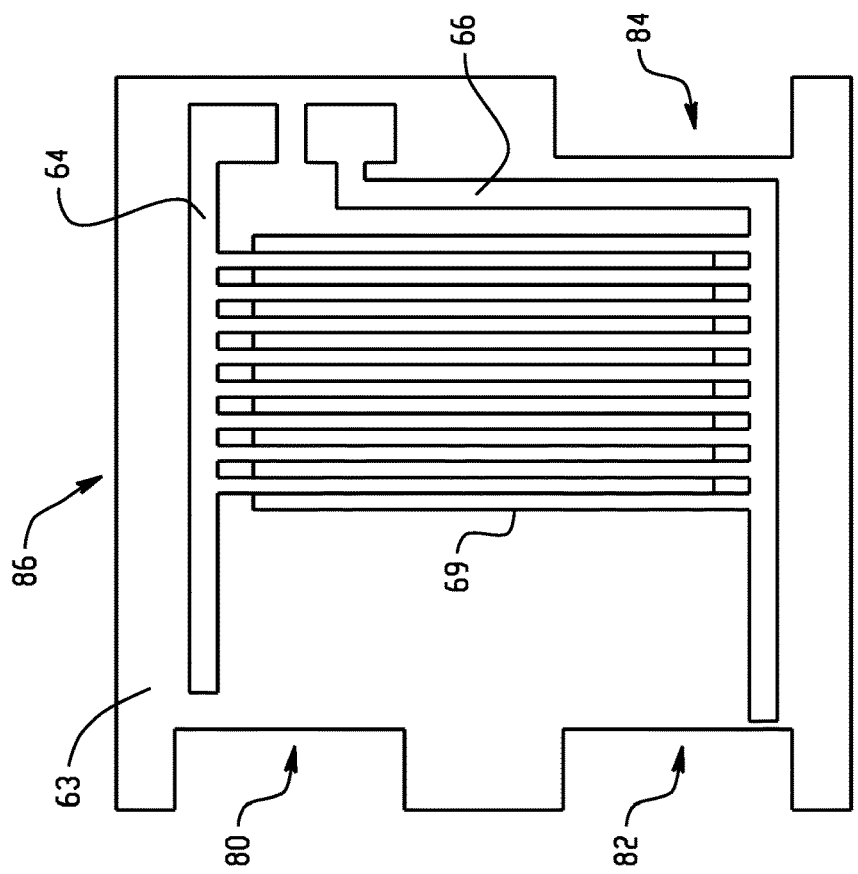

SURFACE ISOLATION RESISTANCE COMPATIBILITY TEST SYSTEM AND METHOD

This application claims the priority of International Application PCT/US2021/034957, filed May 28, 2021, and U.S. Provisional Application 63/032,893, filed Jun. 1, 2020, the disclosures of each of which are incorporated herein by reference in their entireties.

BACKGROUND

The invention relates generally to devices in which deposits form on electrically-conductive components and finds particular application in connection with a system and method for evaluation of deposit formation on electrical components exposed to liquid and vapor-phase lubricants.

Powertrains and other devices in electric vehicles are often lubricated with an oil-based lubricant composition which serves to lubricate moving parts and remove heat. Such compositions may include a lubricating base oil as a major component, and one or more lubricant oil additives, as a minor component, such as antioxidants, detergents, dispersants, antiwear additives, corrosion inhibitors, viscosity modifiers, metal passivators, pour point depressants, seal compatibility agents, antifoam agents, extreme pressure agents, friction modifiers, and the like. Electrical wiring and other current-carrying components of the lubricated device are generally sheathed or coated to minimize contact with the lubricant composition. However, over time, the electrical components may become exposed to the lubricant composition due to wear or heat damage. For example, copper conductors can become overheated, putting stress on the coating, causing it to fail. When this occurs, the lubricant composition can come into contact with the exposed electrical wiring and deposits may form on the wiring. Depending on the chemical nature of the deposits, they may be electrically conducting or non-conducting. Conductive deposits are particularly problematic as they can lead to current flow between closely spaced wires and eventual failure of the electrical device. Additionally, in some components, such as circuit boards, the wiring may be uncoated. These can be exposed to the vapor phase of the lubricant composition and may also suffer deposit formation.

It is to be expected that certain lubricant additives, singly or in combination, may be more prone to cause such deposits in electromechanical devices, such as drivetrains. Further, such devices may be exposed to a vapor phase of the lubricant, which could cause a different type or rate of deposition formation to the liquid phase. However, to date, there has been no method to evaluate lubricant compositions under the conditions commonly experienced in devices which may operate at relatively high temperatures and employing high voltages.

BRIEF DESCRIPTION

In accordance with one aspect of the exemplary embodiment, a system for detecting deposit formation on electrically-conductive materials in vapor and liquid phases includes a test cell for receiving a test liquid, a heater which heats the test liquid to generate a vapor phase of the test liquid in the test cell, a support frame which supports at least a first set of electrical conductors in the test liquid and at least a second set of electrical conductors in the vapor phase, each of the first and second sets of conductors including a live electrical conductor and a neutral electrical conductor. A power source supplies an electric current to each of the live electrical conductors. A sensor component detects an electrical property of each of the sets of conductors, the electrical property changing in response to formation of an electrically-conductive deposit. The sensor component connects the first and second conductors in a respective set of conductors.

In various combinable aspects of the system:

The first and second conductors in each set are supported on a substrate;

The first and second conductors in the first set are supported on a separate substrate from the first and second conductors in the second set;

The first and second conductors in each set are interdigitated on the respective substrate;

The first and second conductors in each set are spaced by a minimum gap;

The minimum gap is at least 0.05 mm;

The change in the electrical property is a drop in electrical resistance;

The sensor component includes a sensor device for each of the sets of conductors;

The sensor devices are located outside the test cell;

The sensor devices include magnetic field based sensors;

The magnetic field based sensors detect a magnetic field generated when an electric current passes through the neutral conductor;

Each set of conductors is integrated into a respective printed circuit board;

The support frame is configured for supporting at least two of the printed circuit boards in the test liquid and a different at least two of the printed circuit boards in the vapor phase of the test liquid;

The test liquid includes a lubricant composition, the lubricant composition comprising an oil as a major component and at least one additive selected from the group consisting of antioxidants, detergents, dispersants, antiwear additives, corrosion inhibitors, viscosity modifiers, metal passivators, pour point depressants, seal compatibility agents, antifoam agents, extreme pressure agents, friction modifiers, and mixtures thereof;

The system includes a data acquisition component, which acquires sensor measurements from the sensor component, and a data processing component, which processes the acquired sensor measurements to generate output information; and/or The output information includes at least one of: an estimate of an amount of deposition for each set of conductors, or for a printed circuit board incorporating the respective set, an estimated rate of deposition for each set of conductors, or for a printed circuit board incorporating the respective set, an estimated time to failure for each set of conductors, or for a printed circuit board incorporating the respective set, a rating for each set of conductors, or for a printed circuit board incorporating the respective set, a comparison between first and second sets of conductors, or between printed circuit boards incorporating the respective sets, and a comparison between first and second test liquids used in respective tests, combinations thereof, and/or information derived therefrom.

In another aspect of the exemplary embodiment, a method for detecting deposit formation on electrically-conductive materials in vapor and liquid phases of a test fluid includes supporting electrical conductors on a support frame in a test fluid, to immerse at least a first set of the electrical conductors in a liquid phase of the test fluid and at least a second set of the electrical conductors in a vapor phase of the test fluid, each of the first and second sets of conductors including a live electrical conductor and a neutral electrical conductor; supplying an electric current to each of the live electrical conductors; detecting an electrical property of each of the sets of conductors, the electrical property changing in response to formation of an electrically-conductive deposit, which connects the first and second conductors in a respective set of conductors.

In various combinable aspects of the method:

The first and second conductors in each set are supported on a same substrate;

The first and second conductors in each set are interdigitated on the substrate;

The first and second conductors in each set are spaced by a minimum gap;

The change in the electrical property is a drop in electrical resistance;

The detecting of the electrical property of each of the sets of conductor comprises measuring a change in a magnetic field generated by the neutral conductors with magnetic field based sensors;

The method further includes integrating each set of conductors into a respective printed circuit board;

The at least a first set of conductors comprises a plurality of first sets of conductors and the at least a second set of conductors comprises a plurality of second sets of conductors and the method comprises supporting the plurality of first sets of conductors and the plurality of second sets of conductors on the same support frame;

The test liquid comprises a lubricant composition, the lubricant composition comprising an oil as a major component and at least one additive selected from the group consisting of antioxidants, detergents, dispersants, antiwear additives, corrosion inhibitors, viscosity modifiers, metal passivators, pour point depressants, seal compatibility agents, antifoam agents, extreme pressure agents, friction modifiers, and mixtures thereof;

The method further includes heating the liquid phase of the test fluid to generate the vapor phase of the test fluid;

The heating of the liquid phase of the test fluid comprises heating the liquid phase to a temperature of at least 100° C., or at least 150° C., or at least 200° C.;

The method further includes acquiring the sensor measurements and processing the acquired sensor measurements to generate output information; and/or The output information includes at least one of: an estimate of an amount of deposition for each set of conductors, or for a printed circuit board incorporating the respective set, an estimated rate of deposition for each set of conductors, or for a printed circuit board incorporating the respective set, an estimated time to failure for each set of conductors, or for a printed circuit board incorporating the respective set, a rating for each set of conductors, or for a printed circuit board incorporating the respective set, a comparison between first and second sets of conductors, or between printed circuit boards incorporating the respective sets, and a comparison between first and second test liquids used in respective tests; combinations thereof, and/or information derived therefrom.

Another aspect includes use of the system for detecting electrically-conductive deposit formation on pairs of electrically-conductive conductors that are contemporaneously exposed to vapor and liquid phases of a test fluid, respectively.

In another aspect of the exemplary embodiment, a combination includes a support frame and a collection of printed circuit boards. The support frame includes a lower portion, which supports a first set of the printed circuit boards, and an upper portion, which supports a second set of the printed circuit boards above the first set of the printed circuit boards, the upper portion being supported on the lower portion. Each of the printed circuit boards includes a live conductor and a neutral conductor, spaced from the live conductor by a minimum gap, which maintains an electrical resistance between the live conductor and the neutral conductor until the gap is bridged by an electrically-conducting deposit.

In one aspect of the combination, at least one of the lower portion and the upper portion includes a biasing member which applies a force to the respective set of printed circuit boards.

In another aspect, a test cell includes the combination and a container for holding a vapor phase and a liquid phase of a test fluid, such that the live conductor and the neutral conductor of each of the first set of printed circuit boards are immersed in the liquid phase and the live conductor and the neutral conductor of each of the second set of printed circuit boards are immersed in the vapor phase.

Another aspect includes use of the test cell for detecting electrically-conductive deposit formation on pairs of electrically-conductive conductors that are respectively exposed to vapor and liquid phases of a test fluid contemporaneously.

BRIEF DESCRIPTION OF THE DRAWINGS

FIG. 3 is a top plan view of another embodiment of a PCB for use in the system of FIG. 1;

FIG. 4 is a top plan view of yet another embodiment of a PCB for use in the system of FIG. 1;

DETAILED DESCRIPTION

Figure 1:
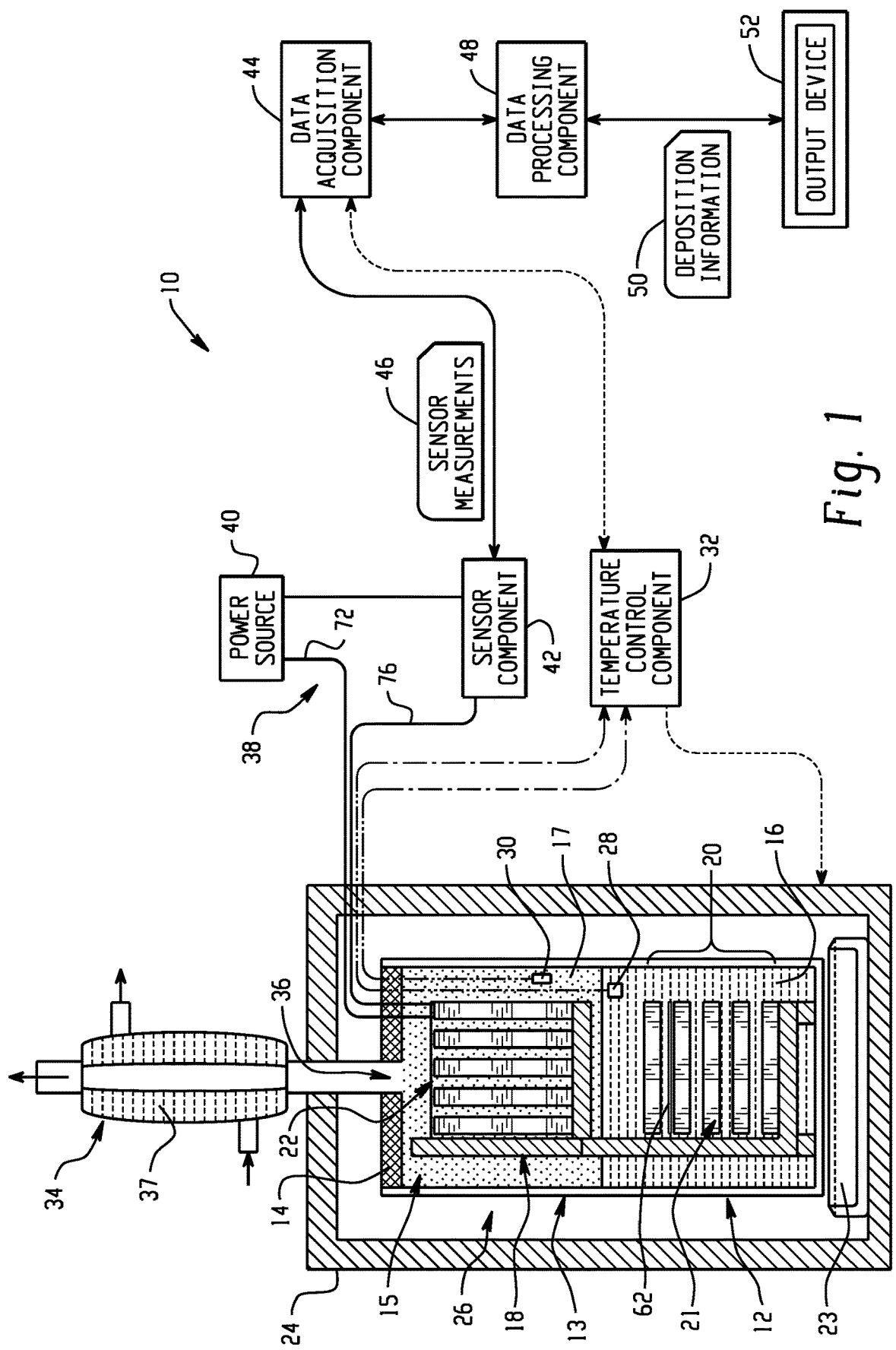
FIG. 1 is a schematic view of a system for evaluating deposit formation on electrically-conductive materials in vapor and liquid phases.

The exemplary embodiment relates to a system and method for evaluating deposits formed on electrical conductors that are exposed to a test fluid, such as a lubricant composition. In the exemplary embodiment, a first set of electrical conductors is exposed to a liquid phase of the lubricant composition while a second set of electrical conductors is contemporaneously exposed to a vapor phase lubricant composition, derived from the liquid phase lubricant composition.

The exemplary lubricant composition may be one of a set of lubricant compositions to be evaluated, e.g., for potential use in a lubricated device in which an electrical conductor may be exposed to the lubricant composition (perhaps through damage to a protective sheathing). Alternatively, or additionally, the current-carrying electrical conductors may be one of a set of electrical conductors of different material compositions and/or configuration types to be evaluated for potential use in a lubricated device.

Example lubricant compositions may include a lubricating organic liquid, such as a base oil of a lubricating viscosity, as a major component, and an additive component, comprising one or more lubricant composition additives, as a minor component, which may be referred to as an additive package. The lubricant composition additive package may include one or more of: antioxidants, detergents, dispersants, antiwear additives, corrosion inhibitors, viscosity modifiers, metal passivators, pour point depressants, seal compatibility agents, antifoam agents, extreme pressure agents, friction modifiers, and the like. Some additives may provide more than one of these functions. Examples of such additives are to be found in U.S. Pub. Nos. 20190367833, by Hanthorn, et al., 20200123463, by Mosier, et al., 20190177649, by Hong, et al., 20170247628, by Cook, et al., 20150038385, by Barton, et al., and 20190249102, by Martin, et al. Suitable oils of lubricating viscosity include natural and synthetic oils, oil derived from hydrocracking, hydrogenation, and hydrofinishing, unrefined, refined, re-refined oils, and mixtures thereof. Examples of unrefined, refined and re-refined oils are described in U.S. Pub. No. 2010197536 and examples of natural and synthetic lubricating oils are described in U.S. Pub. No. 2010197536. Synthetic oils may also be produced by Fischer-Tropsch reactions and typically may be hydroisomerized Fischer-Tropsch hydrocarbons or waxes. In one embodiment oils may be prepared by a Fischer-Tropsch gas-to-liquid synthetic procedure as well as other gas-to-liquid oils. Oils of lubricating viscosity may be as defined as specified in the April 2008 version of "Appendix E-API Base Oil Interchangeability Guidelines for Passenger Car Motor Oils and Diesel Engine Oils", section 1.3 Sub-heading 1.3. "Base Stock Categories". The API Guidelines are also summarized in U.S. Pat. No. 7,285,516 (see column 11, line 64 to column 12, line 10). Other lubricating liquids may also be employed. In one embodiment, the lubricant composition includes at least one of a sulfur-containing additive and a phosphorus-containing additive. The lubricant composition may contain water at less than 10 wt. %, or less than 5 wt. %.

The lubricant composition may be one designed to operate at temperatures in excess of 80° C., or in excess of 100° C., or in excess of 150° C., or in excess of 200° C., or in excess of 250° C., or up to 300° C., for extended periods. The lubricating oil in the lubricant composition may thus have a boiling point, at atmospheric pressure, in excess of 250° C., or in excess of 300° C.

Exemplary materials for forming the electrical conductors include copper, aluminum, gold, nickel, tin, and alloys and mixtures thereof. In one embodiment, the electrical conductors are predominantly copper, e.g., at least 60 wt. % copper or at least 70 wt. % copper. The electrical conductors may be wires with a length many times a cross sectional width, or may be substantially planar printed conductors, optionally with a length many times a cross sectional width.

A first set of conductors in is supported in a liquid phase of a test liquid and a second set of the conductors in a vapor phase of the same test liquid. Each set of conductors includes a live conductor and a neutral conductor, electrically-spaced from the live conductor. When an electrically-conductive deposit forms which connects the live and neutral conductor, a change in an electrical property is detected by a sensor component. In an exemplary embodiment, each set of electrical conductors may be integrated into a respective printed circuit board (PCB) in which a first of the conductors may be energized while a second of the conductors is spaced by a small gap from the first conductor. The second conductor forms an electrical circuit with the first conductor when the resistance between the conductors drops due to formation of conductive deposits on the PCB that extend across the gap.

The exemplary system and method allow investigation of the formation of conductive deposits in energized, non-energized and insulated conductor materials in solution and vapor phases at various electrical power inputs and temperatures using an electromagnetically sensitive sensor component. While the system is capable of operating at low power levels (e.g., about 5 V, 1 mA), it is also capable of operating at higher power levels (e.g., 100-1000V, 1 A-1 kA) that are more representative of real-world lubricated electrical devices used in the automotive industry.

In one embodiment, the system and method provide a comparison of different conductor materials exposed to a lubricant composition in a liquid and/or vapor phase under the same test conditions. In another embodiment, the system and method provide a comparison of a conductor material that is exposed to liquid and vapor phases of the same lubricant composition under otherwise similar or identical test conditions. In another embodiment, the system and method provide for evaluation of different lubricant compositions in the liquid and/or vapor phase in successive tests using the same or different conductor materials.

With reference to FIG. 1, one embodiment of a detection system 10 for detecting deposit formation on electrically-conductive materials in vapor and liquid phases of a test fluid, simultaneously, is illustrated schematically. The system includes a test cell 12, which includes a container 13, such as a glass beaker. The container 13 is substantially closed at an upper end by a removable closure 14, such as a joint clip, stopper with bores, or the like. The container 13 defines an interior chamber 15, which holds a test liquid 16, such as a lubricant composition, and a vapor 17, derived from the test liquid 16, which is in contact with the test liquid 16.

A support frame 18, within the test cell container 13, supports a collection of printed circuit boards (PCBs) 21, such as 4, 8, 12, 16, or more PCBs 21. A first set 20 of the PCBs is immersed solely within the liquid 16, and a second set 22 of the PCBs is positioned solely within the vapor 17, when it is formed. In other embodiments, separate support frames may be used for the first and second sets 20, 22 of printed circuit boards. The first set 20 of PCBs 21 may be arranged in parallel and optionally stacked vertically (one on top of the other). The second set 22 of PCBs may be arranged in parallel, and optionally stacked horizontally (side by side). The support frame 18 may be configured to maintain the orientations and/or spacing of the PCBs 21 throughout a test. The support frame may be positioned on a shelf 23, such as a drip tray, positioned on the base of the oven.

The liquid 16 is heated by a heater 24. In one embodiment, the test cell 12 is positioned within a heated chamber 26, e.g., defined by a heating device, such as an electric oven 24. However other types of heater are contemplated, such as an oil bath, electrical heating tape, or the like. Temperature sensors 28, 30, such as platinum resistance thermometers (PRTs), monitor the temperature of the test liquid 16 and vapor 17, respectively. A temperature control component 32 receives signals from the temperature sensors 28, 30 and, based on the received signals, controls the heating device 26 to maintain the chamber 24, and hence the liquid 16 and vapor 17, at a preselected temperature or temperatures. For example, the temperature of the heated liquid 16 may be at least 100° C., or at least 150° C., or at least 200° C., such as up to 300° C., or about 250° C. In one embodiment, wiring for the PRTs 28, 30 may be carried through a bore or bores (not shown) in the removable closure 14.

The test cell 12 may be vented to atmosphere, e.g., through a condenser 34, which is fluidly connected with an upper opening 36 in the test cell defined by the removable closure 14. The condenser 34 may be a liquid-type condenser in which, liquid (e.g., water), at a temperature below that of the vapor, is flowed through a cooling jacket 37. Vapor is thereby condensed and returned to the chamber 15. Alternatively, the condenser 34 may be a findenser in which a ring of metal fins replaces the cooling jacket. In the illustrated system, the vapor pressure within the chamber 15 is at or slightly above atmospheric pressure. In another embodiment, a pressure relief valve (not shown), set at a pressure above atmospheric, may be disposed in fluid connection with the outlet 36 to maintain the vapor 17 at a selected pressure which is above atmospheric pressure. In one embodiment, wiring for the PRTs 28, 30 may be carried through the outlet 36.

The detection system 10 further includes an electrical circuit 38, which electrically connects a power source 40 with each of the PCBs in sets 20, 22. The power source 40 may be an AC or a DC power source. In one embodiment, the power source 40 generates a current/voltage comparable to that used in an electric vehicle component, such as an electric motor or transmission system. While a single power source 40 is used in the illustrated embodiment, in other embodiment, two or more power sources 40 may be used, each of the power sources forming a circuit with a respective one or more of the PCBs. In this case, the power sources may be the same or different.

Figure 5:
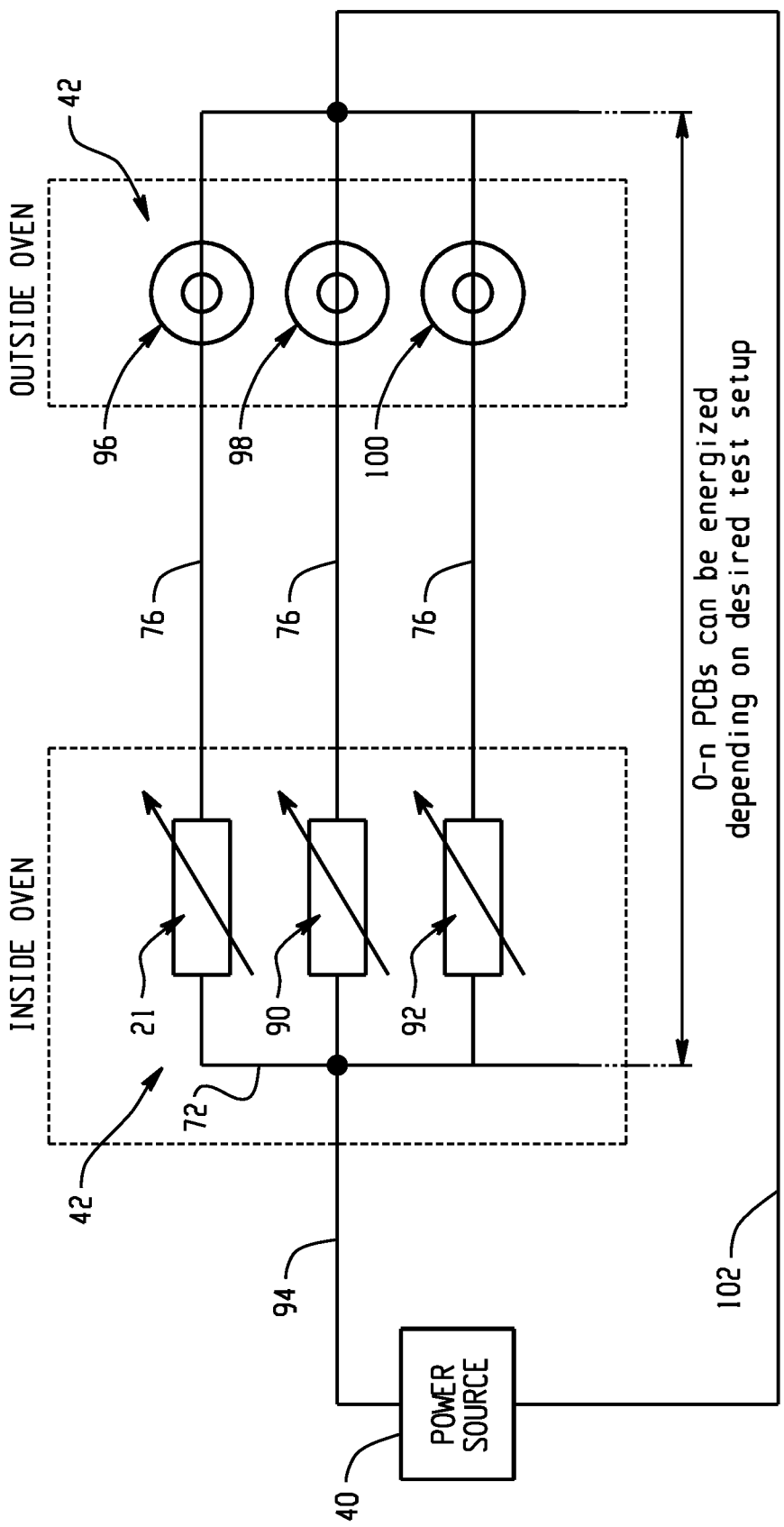
FIG. 5 is a schematic circuit diagram showing sensors for evaluating resistance changes of PCBs in the system of FIG. 1.

A sensor component 42 is positioned to detect changes in an electrical property of each of the PCBs 21, or other measurable property which is a function thereof. The change in the electrical property of each PCB is primarily caused by the formation of deposits from the respective test liquid or its vapor. The electrical property may be electrical resistance, electrical current flow, or voltage, as described in further detail below. The sensor component 42 may be external to the test cell 12, as illustrated in FIG. 5. The sensor component outputs sensor measurements 46 for each PCB that correlate with the change in the electrical property of that PCB.

The system 10 further includes a data acquisition component 44, which periodically acquires and stores sensor measurements 46 generated by the sensor component 42, and a data processing component 48, which processes the sensor measurements 46 to generate output information 50.

The output information 50 may be output to an output device 52, such as a display device, memory storage device, printer, combination thereof, or the like, optionally after further processing. The information may be stored or displayed in tabular form, as a graph or chart, or in any other suitable format.

As will be appreciated, some of the illustrated components 32, 40, 42, 44, 48, 52 of the system 10 may be separate or combined. Each of these components may be controlled by a separate processor, based on software instructions stored in an associated memory device, or two or more of the components may be controlled by a common processor. The processor may be any hardware device(s) suitable for performing the instructions, such as a CPU, microprocessor, or the like. The associated memory may include RAM, ROM, or a combination thereof.

Figure 2:
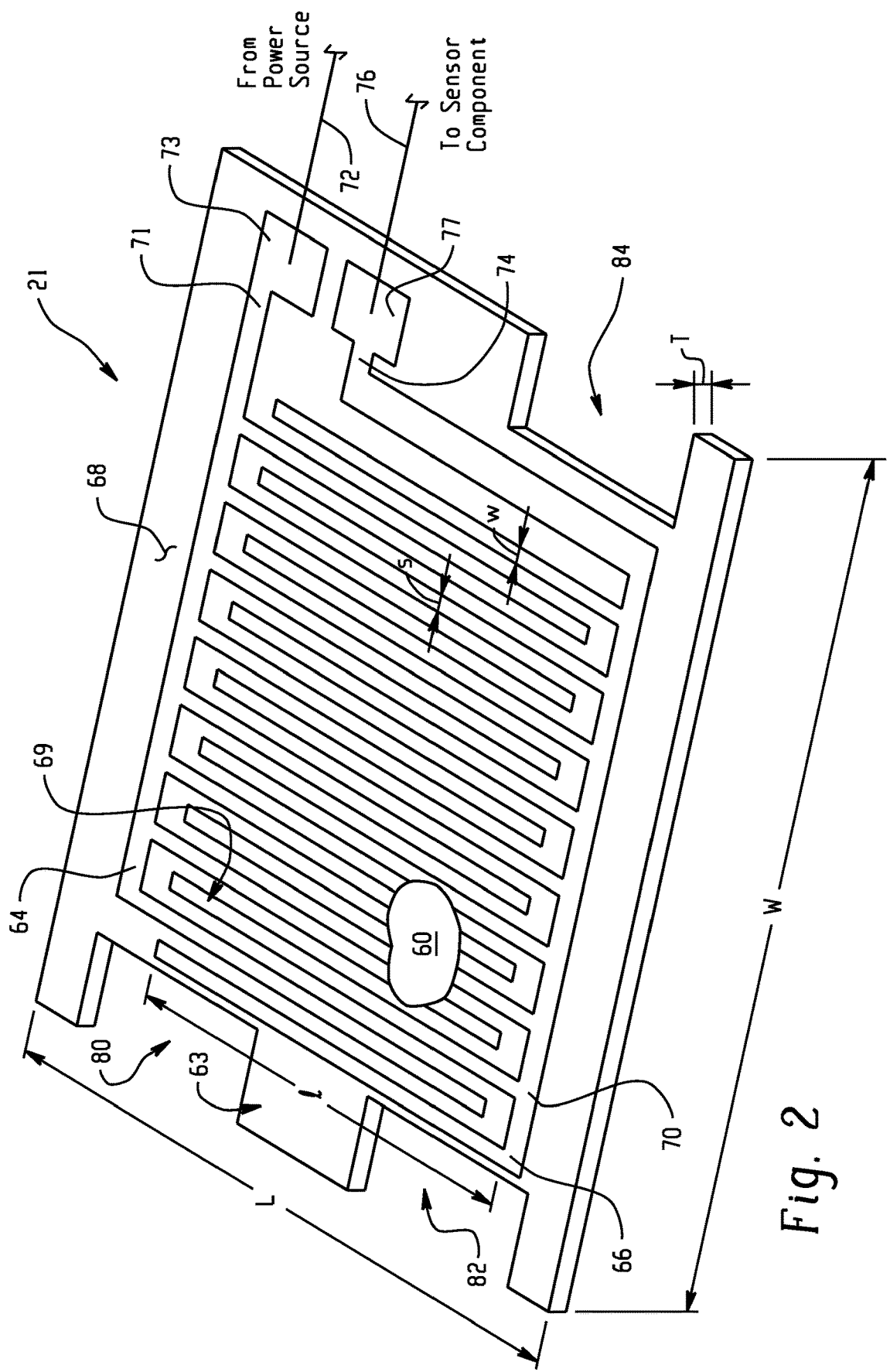
FIG. 2 is a perspective view of one embodiment of a printed circuit board (PCB) for use in the system of FIG. 1.

With reference also to FIG. 2, an exemplary PCB 21 is shown. Each set 20, 22 of PCBs may include one, two, three or more of PCBs 21, such as up to 10 (each stack includes five PCBs in the embodiment of FIG. 1). The PCBs serve as variable resistors whose resistance changes in response to the build-up of conductive deposits 60 from the surrounding vapor or liquid. While the illustrated PCBs 21 in stack 20 are arranged horizontally, in parallel, it is to be appreciated that the PCBs may be arranged vertically or in another orientation. Similarly, while the illustrated PCBs 21 in stack 22 are arranged vertically, in parallel, it is to be appreciated that the PCBs may be arranged horizontally, or in another orientation.

In some embodiments, adjacent PCBs 21 in a set 20, 22 are spaced primarily by the liquid/vapor in which they are immersed. In other embodiments, a layer 62 (FIG. 1) of insulating material (such as Nomex Paper) can be placed over one or more of the PCBs to investigate the effects of trapped lubricant underneath the layer of insulating material and the consequence this has on the formation of conducting layer deposits.

With continued reference to FIG. 2, each PCB 21 includes a non-conductive substrate 63 (an electrical insulator) on which first and second electrical conductors 64, 66 are laid on a same surface 68 of the substrate, e.g., by printing or other deposition technique. Suitable materials for forming the substrate 63 include fiberglass, polytetrafluoroethylene (Teflon®), ceramics and certain polymers. One example is FR-4, which is a fiberglass-epoxy laminate. The illustrated substrate is generally rectangular, with a (maximum) width W equal to a (maximum) length L and a thickness T which is substantially less than the width and length. One of the conductors (e.g., conductor 64) may be a live conductor, receiving power from the power source, while the other of the conductors (e.g., conductor 66) is a neutral conductor, which carries current from the PCB, but only when an electrically-connecting deposit 60 forms. In one example embodiment, W=L=3-20 cm, e.g., at least 5, or at least 8 cm. T may be 0.5-5 mm.

The illustrated conductors 64, 66 in FIG. 2 each include a set of parallel fingers 69, such as at least five or at least ten fingers, which extend perpendicularly from a common portion 70 (bus bar) of the respective conductor. Each conductor 64, 66 may have at least 2 fingers, or at least 5 fingers, such as up to 120 fingers, or up to 20 fingers (the total number of fingers per PCB is approximately double these numbers). The fingers 69 of the first conductor 64 are interdigitated with the fingers of the second conductor 66. A fixed spacing s is provided between adjacent fingers. However, other arrangements which provide such a uniform spacing s between conductors are also contemplated. In other embodiments, each conductor has only one "finger" and thus there is no interdigitation.

In one embodiment, each of the first and second conductors 64, 66 is of a fixed length, e.g., at least 20 cm, such as a 1 meter length of circuit wiring. In one embodiment, the fingers have a same width w (in the W direction) of 5 mm or less, e.g., 2 mm or less, or 1.5 mm, or less, such as at least 0.5 mm. In one embodiment, the fingers are 1 mm in width. In one embodiment, the fingers have a same length l' (in the L direction) of 50 mm or less, e.g., 30 mm, or less, such as at least 10 mm. The spacing s (in the W direction) between each two adjacent fingers of the different conductors may be 2 mm or less, e.g., 1.5 mm, or less. In one embodiment, the fingers are 1 mm apart. In another embodiment, the fingers are at least 0.05 mm apart, or about 0.1 mm apart. In the embodiment of FIG. 2, the spacing s is accomplished by two interlocking comb style patterns that do not connect.

The common portion 70 of the first conductor 64 is connected at a first end 71 to the power source, e.g., by a first electrically-conductive connection line, such as a wire (live) 72, which may be soldered to a solder pad 73 at the end 71 of the conductor 64. The common portion 70 of the second conductor 66 is connected at a first end 74 to a second electrically-conductive connection line, such as a wire 76 (neutral), which may be soldered to a solder pad 77 at the end of the conductor 66. In one embodiment, the second connection wire 76 leads to the sensor component 42. The connection lines 72, 76 may at least partially be sheathed by an electrically-insulative material, to reduce stray currents near the PCB. In an exemplary embodiment, the conductors 64, 66 are not sheathed or coated, such that the metal of each conductor is directly exposed to the lubricant composition during the test. However, it is also contemplated that one or both conductors 64, 66 may alternatively be sheathed and/or coated with an electrically insulative material, which may become dislodged or otherwise at least partially removed to expose the conductor(s) during a test.

When the PCB 21 is first installed in the test cell 12, there is no (or substantially no) electrical connection between the first and second electrical conductors 64, 66, since the substrate 63 is formed from an electrically insulative material, the conductors 64, 66 are spaced by a minimum gap s, and the lubricant composition has a low electrical conductivity. When exposed to the hot lubricant liquid or vapor, however, electrically-conductive deposits can build up over the surface 68, bridging the gap s between the conductors at one or more locations. This results in a change in an electrical property of the PCB. In particular, a drop in resistance occurs between the first and second electrical conductors 64, 66. As a result, current flows through the neutral wire 76, which is detected by the sensor component 42. Depending on the desired test, any number of PCBs can be energized by the same or different power sources 40, from zero up to the maximum holding capacity of the support structure 18 and within the limitations of the power source(s) 40.

For ease of stacking the PCBs, the substrate 63 may be generally rectangular or square, and include one or more equally-sized cutouts 80, 82, 84. Three cutouts, as shown, allow multiple boards 21 to be stacked in different orientations while maintaining space above each board's solder pads 73, 77 for the wiring 72, 76 to connect to it.

FIGS. 3 and 4 illustrate alternative PCBs 86, 88 which may be similarly configured to PCB 21, except as noted. In FIG. 3, the spacing s (which is too small to illustrate) between the adjacent fingers 69, defined by the conductors 64, 66, is 0.1 mm, or less, as compared to 1 mm in FIG. 2, while the overall length of the conductors remains the same. The conductors thus occupy a smaller region of the substrate surface 68. The substrate 63 is the same size and shape as that of FIG. 2, allowing different configurations of PCB to be stacked in the same set/support frame. In FIG. 4, the spacing s between adjacent fingers 69 is 1 mm and the two fingers are much wider (larger w), although shorter in length l, than the embodiments of FIGS. 2 and 3, thereby maximizing the area of the substrate occupied by the conductors 64, 66. In the embodiment of FIG. 4, the conductors are not interdigitated.

With reference also to FIG. 5, a wiring diagram illustrates connections for three illustrative PCBs 21, 90, 92. Each of PCBs 21, 90, 92 may be similarly configured. Alternatively, one or more of the PCBs 21, 90, 92 may have a different configuration, as illustrated, for example, in FIGS. 2, 3 and 4, or may differ in terms of the conductor compositions. While three PCBs are shown in FIG. 5 for illustration, any number of PCBs can be arranged in parallel. Additionally, one or more PCBs in a set 20, 22 may be non-energized, e.g., to allow a comparison between energized and non-energized PCBs.

The energized PCBs 21, 90, 92 are connected in parallel with the source 40. To enable this, a common live conductor wire 94 is electrically connected to the power source 40 and to the respective live conductor wire 72 of each PCB to energize the PCBs. The neutral wire 76 for each energized PCB is independent, but the live wire 72 is common. The neutral wire 76 from each PCB leads to the sensor component 42. In the illustrated embodiment, the sensor component 42 includes a respective sensor device 96, 98, 100 for each neutral wire 76. Each sensor device outputs a measure of an electrical property of the respective PCB. The neutral wires 76 are each connected, downstream of the sensors, to the power supply 21, by a common neutral wire 102. Each sensor device 96, 98, 100, may be located in proximity to the respective neutral line 76, and feed a proportional signal to the data acquisition component 44. This arrangement allows for independent measurement of each energized PCB and is both non-invasive but can also allow the sensor devices to be located outside the oven in a controlled environment.

Figure 6:
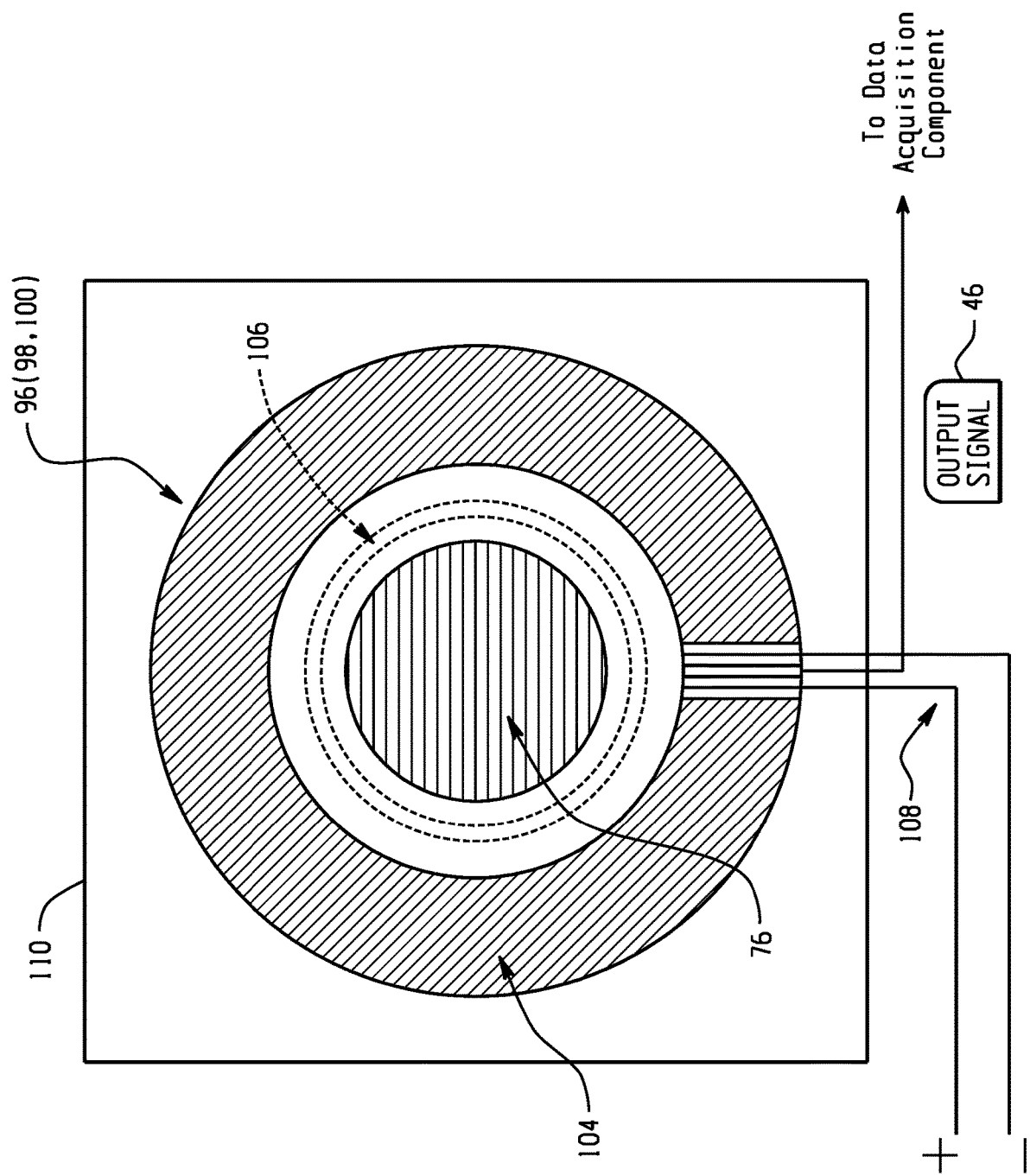
FIG. 6 is a top plan view of one of the sensors of FIG. 5.

The exemplary sensor devices 96, 98, 100 may be magnetic field based sensors which each output a proportional signal to the data acquisition component 44. For example, as illustrated in FIG. 6, each sensor device 96, 98, 100 is a Hall effect sensor, specifically, a Ferrite toroid Hall effect sensor, with a magnetically-permeable core 104. The neutral wire 76 passes axially through the core. Current flowing through the neutral wire 76 generates a magnetic field 106, which is detected by an electrically powered sensor circuit 108. The sensor circuit 108 converts the magnetic field to a corresponding resistance or electrical current signal 46, which is output to the data acquisition component. The resistance/electric current signals 46 may be acquired periodically, e.g., every second, or every 10 seconds, or every 10 hours, or every 50 hrs. A complete test may include acquiring sensor measurements for a period of minutes, hours, or days, such as at least 300 hrs, or at least 500 hrs, depending on the test conditions and/or the rate of deposit formation on the PCBs.

The exemplary sensor devices 96, 98, 100, etc. are powered independently of the PCB source with each sensor individually sited in a shielded enclosure 110. The shield 110 helps to stop stray fields interfering with the signal of interest, but also to serves prevent interference with other electro-magnetic signals.

Figure 7:
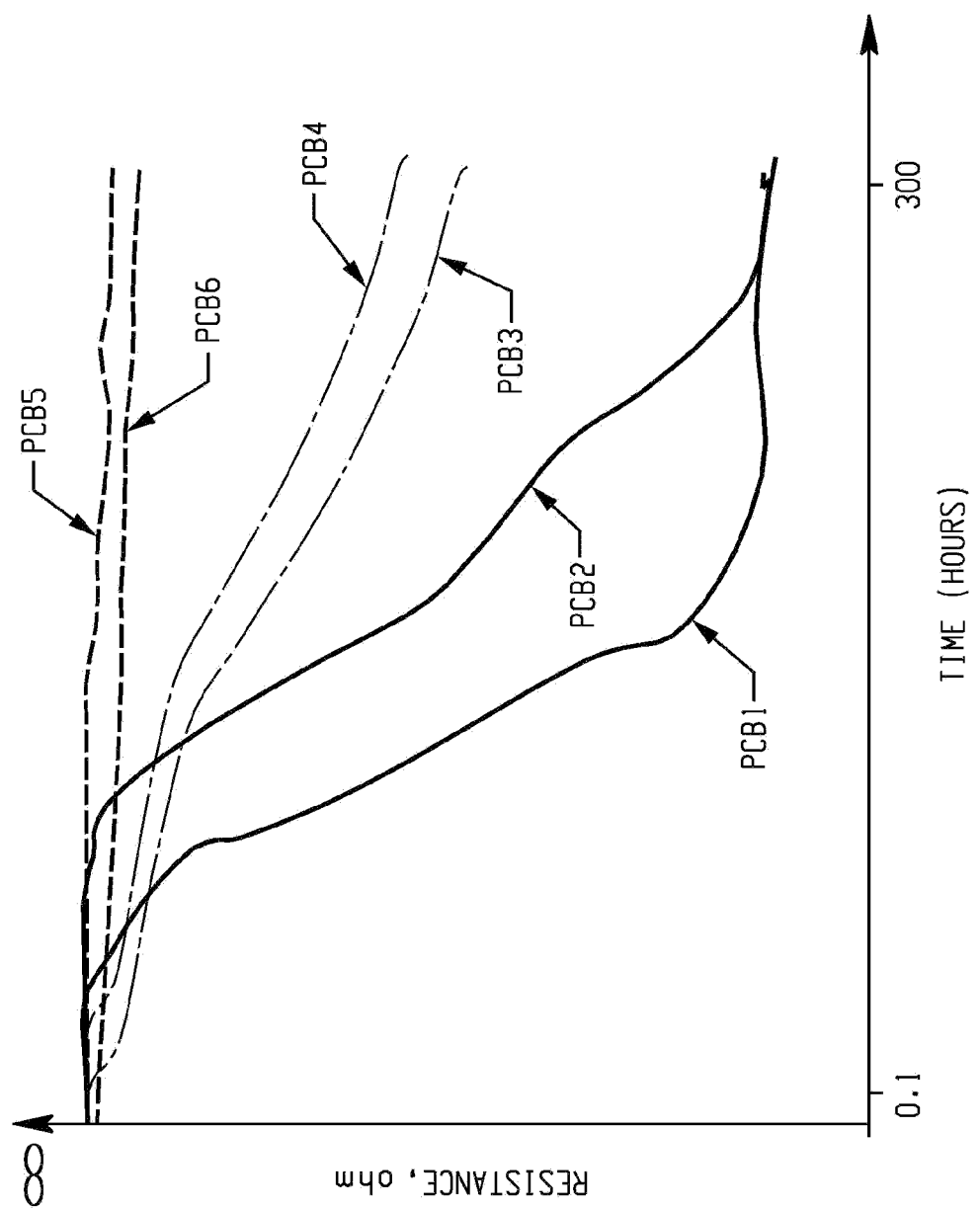
FIG. 7 is plot, intended for illustration only, showing how resistance could change in a set of PCBs undergoing testing in the system of FIG. 1.

The electric current passing through the neutral wire 76 increases as electrically conductive deposits build up on the respective PCB. The output resistance signal 46 thus decreases in proportion to the current passing through the wire. For example, FIG. 7 illustrates a graph of resistance signals 46 which could be generated over time by the data processing component 48 for six exemplary PCBs. As will be appreciated, the graphs could illustrate increasing current flow over time, rather than decreasing resistance. For example, graphs denoted PCB1 and PCB2 could be for identically-configured PCBs in the set 20 exposed to the liquid lubricant composition, while PCB3 and PCB4 could be for identically-configured PCBs in the set 22 exposed to the vapor form of the lubricant composition (FIG. 1). PCB5 and PCB6 could represent non-energized PCBs (in the liquid or vapor). As will be appreciated, the output of the data processing component 48 could alternatively or additionally be averaged over the energized (non-energized, respectively) PCBs in the set 20, 22, or expressed in some other form, such as average time to reach a selected signal value, or the like.

Other magnetic field-based sensors (magnetometers) may be used as the sensor devices 96, 98, 100, depending on the type of power supplied to the PCB (AC or DC) as well as to optimize signal sensitivity. For example, inductive sensors (which include a wire wrapped round a magnetically permeable core), Fluxgate Magnetometers (which include a transducer for converting magnetic field to a voltage), and/or Magnetoresistance-based sensors (which measure the change in resistance in a disk through which current is flowing, as a result of a magnetic field) may be used.

Other suitable sensors which may be used include Eddy Current based displacement sensors and Potential Voltage measurement techniques. Eddy Current sensors are based on the principle that a changing magnetic field will induce Eddy currents in a targeted conductive material. These Eddy currents produce a magnetic field in opposition to the original field which is detected by the Eddy current sensor. Whilst typically used for distance (displacement) measurements and flaws in materials, they can be used for detecting changes in material thickness as a growth in a conductive material will be detected as a change is distance from the face of the sensor to the conductive material which in this case would be the conductive layer.

While in the illustrated embodiment, the sensor component 42 is located outside the test cell 12, in another embodiment, sensor devices may be positioned within the test cell.

Figure 8:
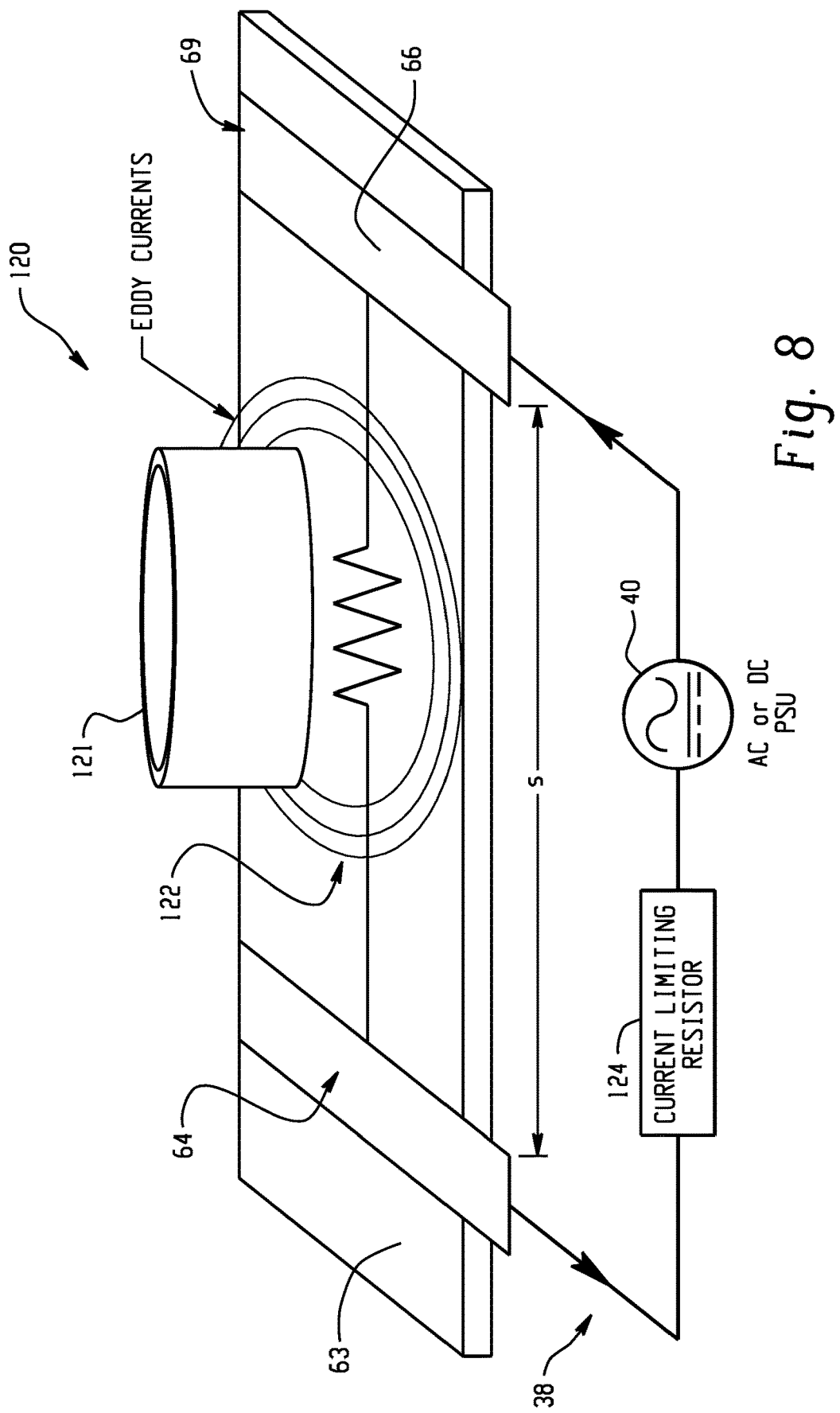
FIG. 8 illustrates another embodiment of a sensor for use in the system of FIG. 1.

FIG. 8 illustrates an example eddy current sensor device 120, which may be used within the test cell 12. The sensor device 120 includes a hollow metal core 121, which is positioned at a fixed height above the gap s between adjacent fingers 69. Eddy currents form when a dendrite 122 of the conductive deposit (illustrated as a resistor) extends between two adjacent fingers 69, allowing current to flow between them. The sensor device 120 detects the eddy current and sends signals derived therefrom to the acquisition component 44. A current limiting resistor 124 may be incorporated in the circuit 38.

Figure 9:
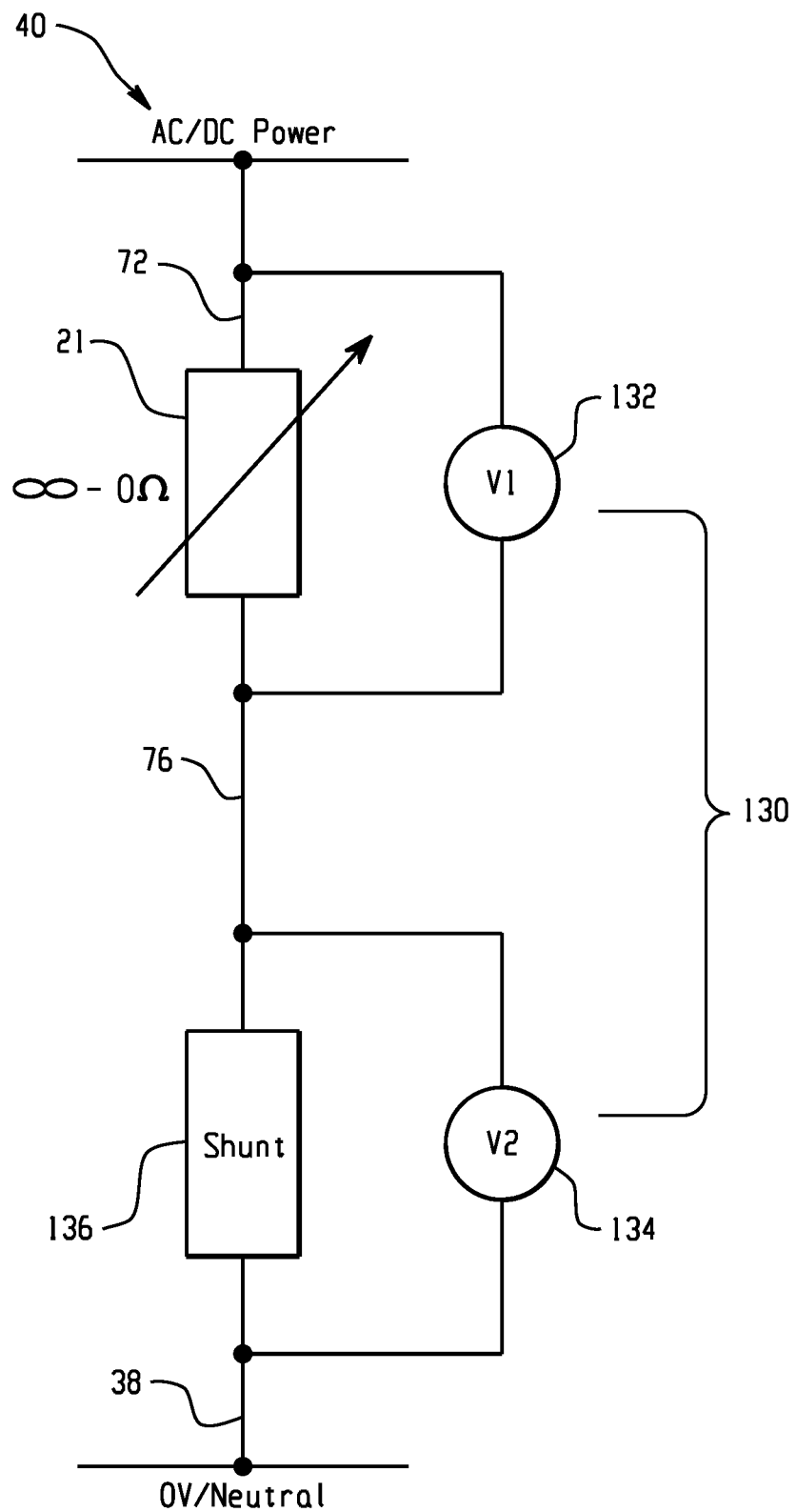
FIG. 9 illustrates yet another embodiment of a sensor for use in the system of FIG. 1.

An example Potential Voltage sensor device 130 is illustrated in FIG. 9 and includes voltmeters 132, 134, denoted V1 and V2. Each PCB 21 acts as a variable resistor whose resistance can range from zero ohms to an infinite (or very high) resistance. The voltage across the PCB 21 is measured by voltmeter V1. The circuit 38 also includes a shunt resistor 136, which generates a potential voltage based on the current flowing through the circuit. The voltage is measured by voltmeter V2. Ohms law can then be applied to calculate the resistance of the PCB 21.

In particular, if a voltage $v_2$ is measured across a shunt 136 having resistance $r_2$, the current i flowing through the circuit is:

$$i = \frac{v_2}{r_2} \quad (1)$$

The resistance $r_1$ across the PCB is then:

$$r_1 = \frac{v_1}{i},$$

where $v_1$ is the voltage measured by V1.

One problem with the Potential Voltage method is that it causes perturbations with the applied power source signal due to the shunt resistor 136. The shunt resistor 136 is usually of small resistance value. However, as the resistance of the PCB reduces, more current flows, which forces more of the applied voltage to be dropped across the shunt resistor.

Any suitable data acquisition and processing devices may be employed for components 44, 46. The software that controls the data acquisition and control hardware may be based on LabVIEW™ and configured for acquiring data from multiple sensor devices contemporaneously or in quick succession. The acquired data may be processed to generate a desired output and stored in a suitable data structure, such as a table, database, or the like.

Figure 10:
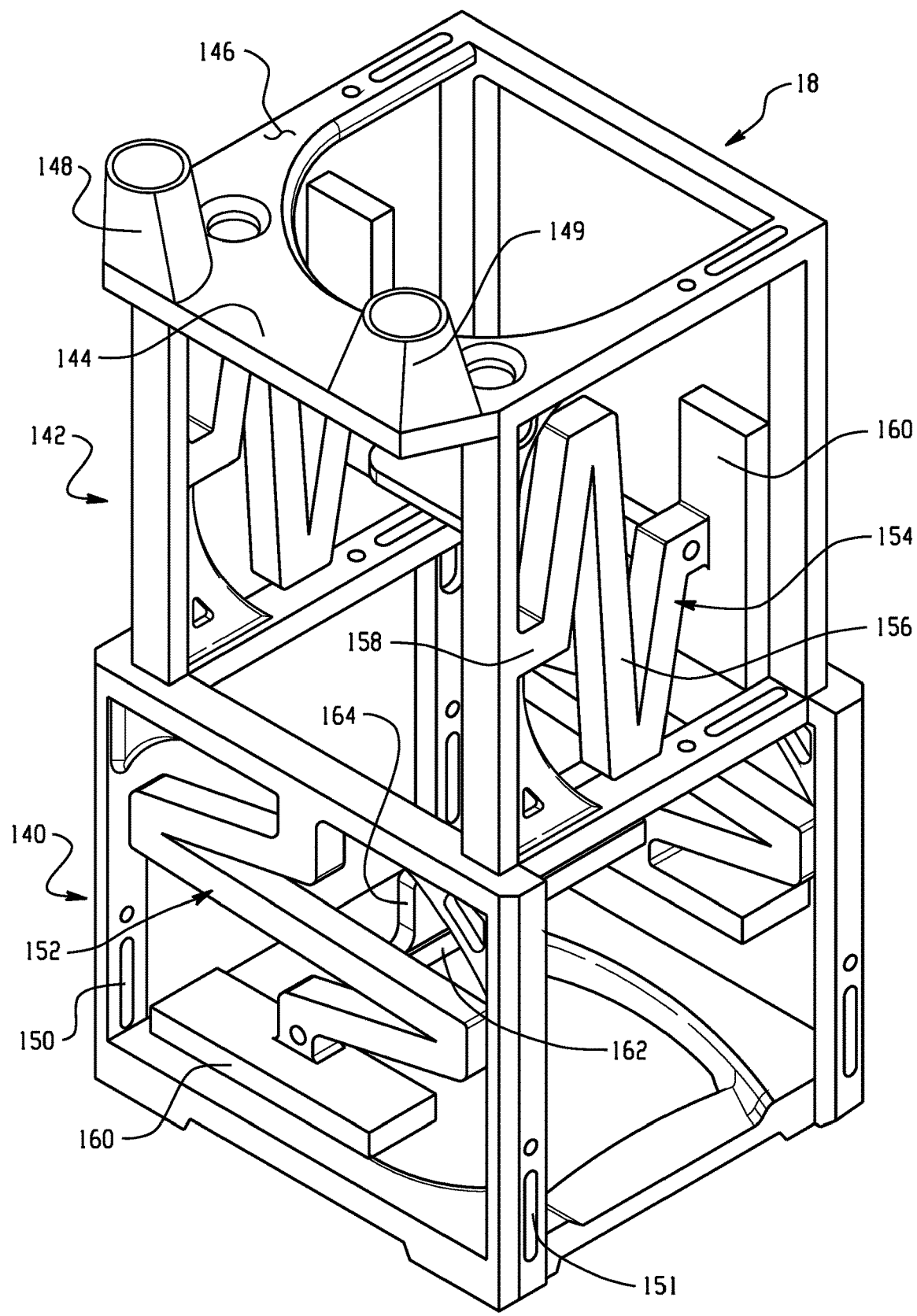
FIG. 10 is a perspective view of a support frame suitable for use in the system of FIG. 1.
Figure 11:
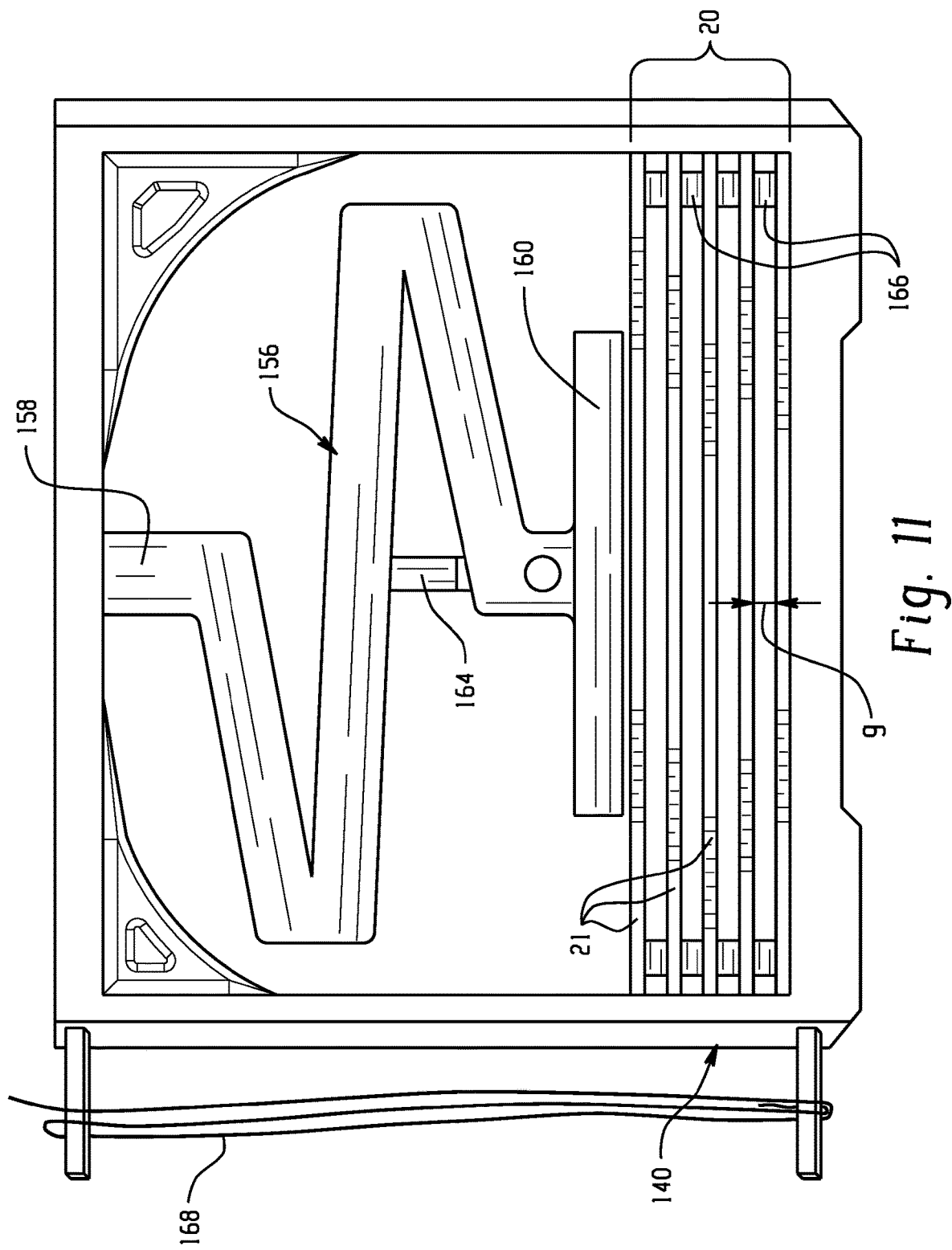
FIG. 11 is a side sectional view of a lower portion of the support frame of FIG. 10.
Figure 12:
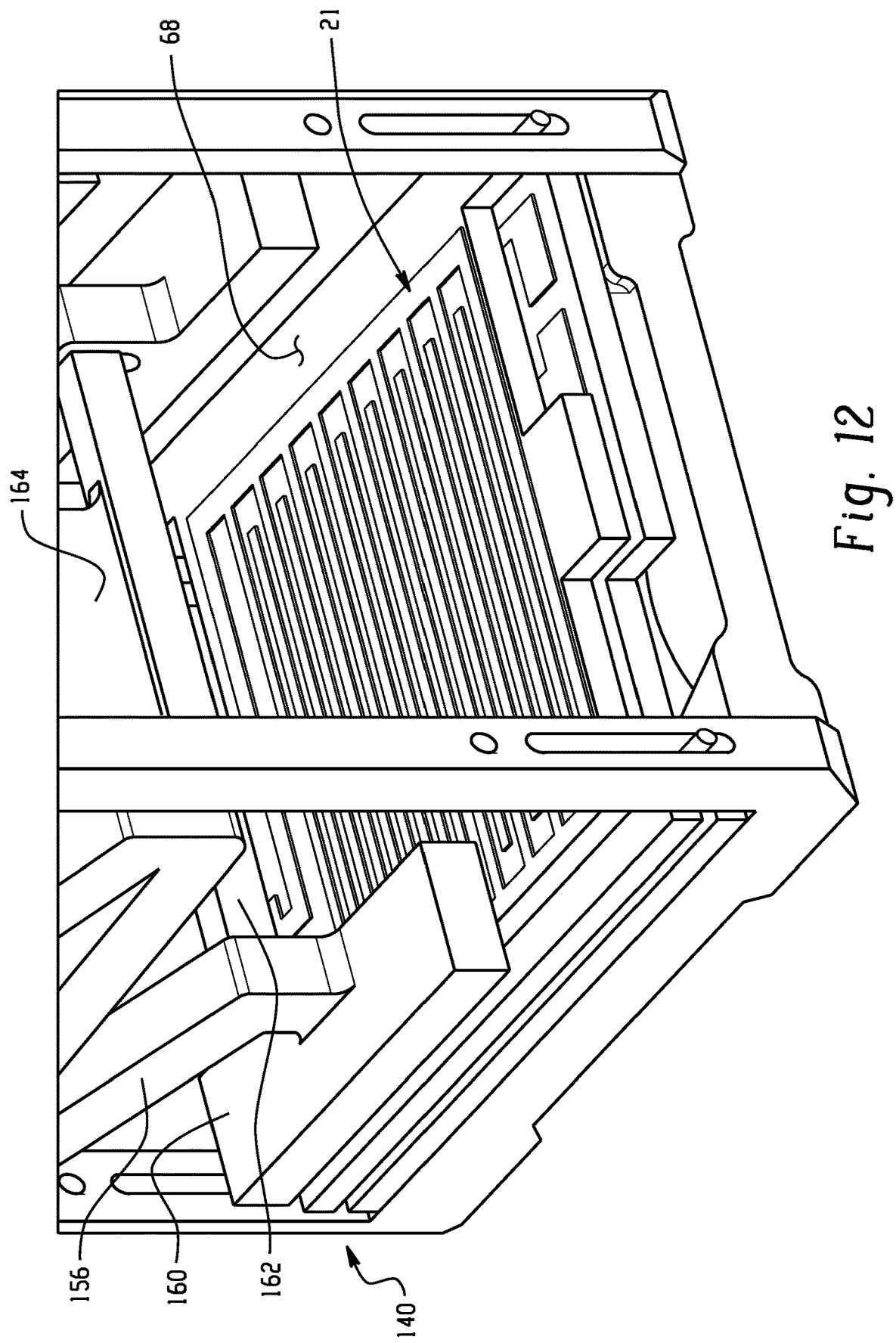
FIG. 12 is a perspective view of the lower portion of the support frame of FIG. 10.

With reference now to FIGS. 10-12, one embodiment of a support frame 18 is illustrated, which is suited to use in the system of FIG. 1. The support frame includes a lower structure 140, for supporting the first set 20 of PCBs, and an upper structure 142, for supporting the second set 20 of PCBs. The lower and upper structures 140, 142 may be locked or otherwise maintained in their relative positions during a test by fixing members, such as clamps, screws, adhesive, or the like. Alternatively, the lower and upper structures 140, 142 may be integrally formed. The lower and upper structures 140, 142 have openings on their six sides to allow for free flow of liquid/vapor respectively. A flange 144, extending from an upper surface 146 of the upper structure 142 includes collars 148, 149 for carrying electric wires 94, 102 to and from the PCBs. Various apertures 150, 151, etc., through the support structure may be used to feed the wires 72, 76 between the PCBs and the collars.

Each of the structures 140, 142 supports a biasing member 152, 154, which maintains a pressure on the respective set 20, 22 of PCBs during a test. This ensures that the spacing between each pair of PCBs is the same and remains constant throughout the test. In the illustrated embodiment, each of the biasing members 152, 154 includes two spaced flexible arms 156 that act as springs. One end 158 of each arm 156 is connected to the respective support structure 140, 142, while the other terminates in a flat plate 160, which maintains tension on the stack 20, 22 in their desired orientation (FIGS. 11 and 12). The illustrated arms 156 are zigzag-shaped pieces of metal or plastic that that are compressible to allow the PCBs 21 to be inserted and removed from the support frame 18. The arms 156 may be interconnected by a strut 162 near their terminal ends to limit relative movement of the arms (FIG. 12). In one embodiment, a plate 164 (FIG. 11) extends from the strut for ease of lifting the biasing member 152, 154 away from the PCBs.

Spacers 166 may be positioned in between the PCBs to maintain a fixed gap g between the PCBs, when compressed by the biasing member (FIG. 11). For example, 1 mm spacers may be used. In some embodiments, the spacers are in the form of posts attached to each PCB.

Figure 13:
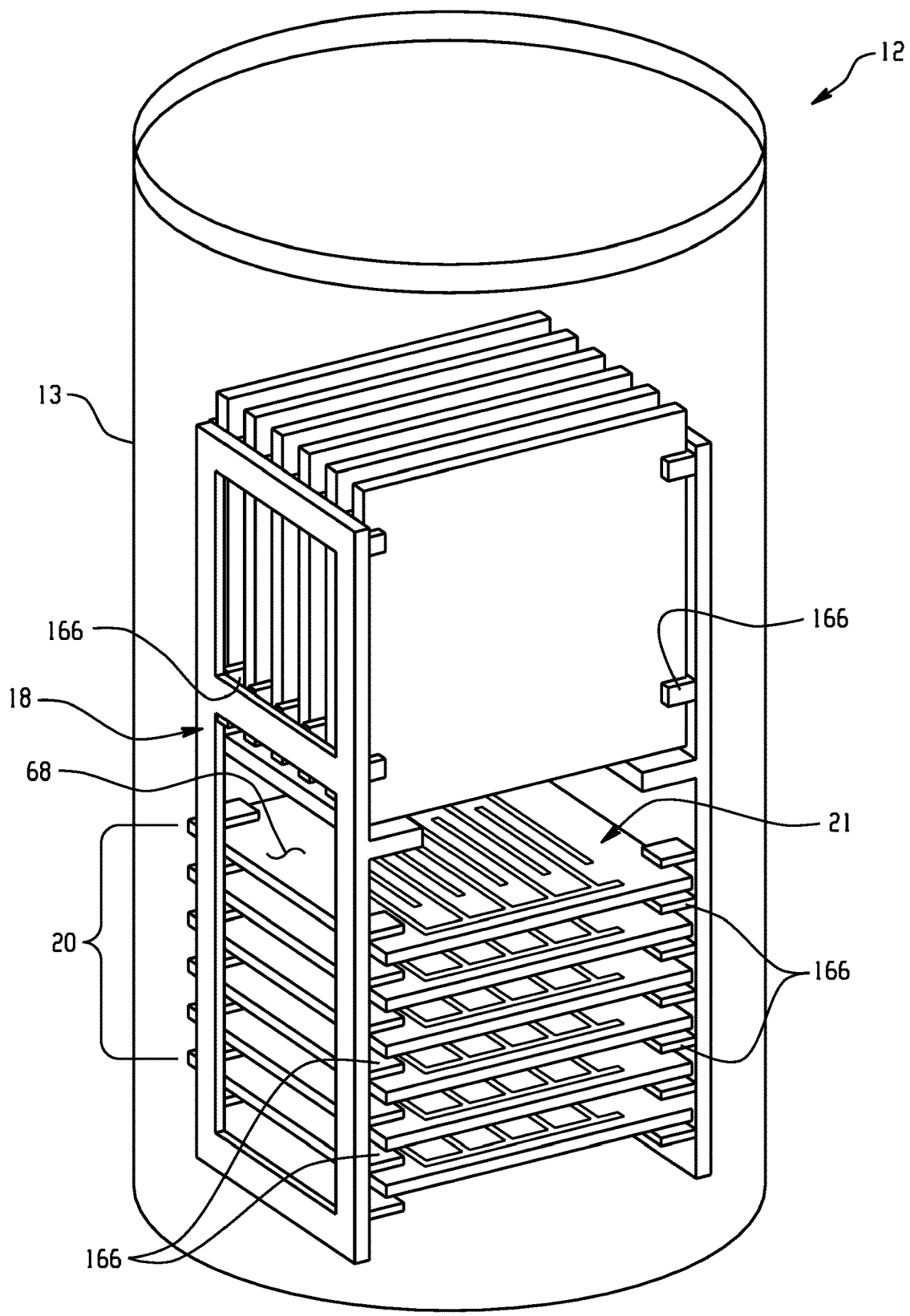
FIG. 13 is a perspective view of a test cell incorporating another embodiment of a support frame suitable for use in the system of FIG. 1.

With reference now to FIG. 13, another embodiment of a support frame 18 is illustrated. The support frame is configured similarly to the support frame of FIGS. 10-12, except as noted. In particular, the biasing members are omitted. Spacers 166 are positioned between the PCBs to maintain a fixed minimum gap g. The spacers are in the form of posts attached to the support frame.

In some embodiments, the support frame 18 may be also configured to support a conductive metal wire 168 that is used for measuring a rate of corrosion of the wire in the liquid or vapor (FIG. 11). Such a wire may be of a fixed length. A first wire 168 may be supported on the lower part of the frame 18 such that it is only immersed in the liquid while a second wire (not shown) may be supported on the upper part of the frame such that it is only within the vapor. Corrosion of the wire 168 may be determined from a change in resistance of the wire during a test since corrosion reduces the cross-sectional area of the wire which, in turn, affects the resistance.

Figure 14:
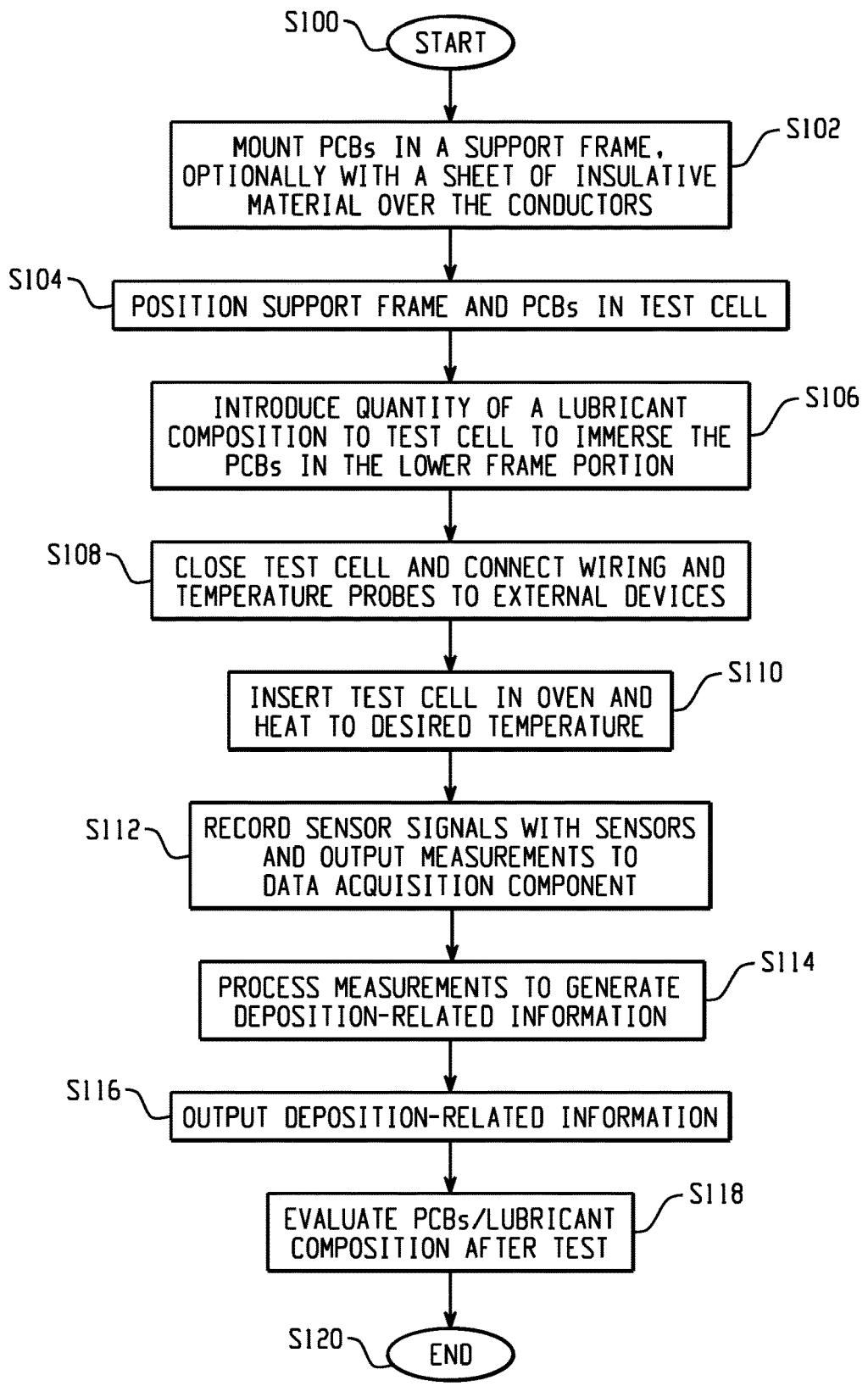
FIG. 14 is a flow chart illustrating a test method which may be performed with the system of FIG. 1.

With reference now to FIG. 14, a method for evaluating deposits on electric conductors is illustrated. The method can be performed with the system of FIG. 1, using PCBs as illustrated in one or more of FIGS. 2-4, sensors as illustrated in one or more of FIGS. 5-6 and 8-9, and a support frame or frames as illustrated in one or more of FIGS. 10-13. However, other systems in which sets of conductors are positioned in the liquid and vapor phases are also contemplated for use in the method. The method begins at S100.

At S102, sets of electrically-spaced conductors are mounted in a support frame 18 or frames. The sets of conductors may be in the form of PCBs such that a first of the sets 20 of PCBs will be positioned in a liquid lubricant composition and a second on the sets 22 will be positioned in the vapor phase, above the liquid lubricant composition. Each PCB in a set faces the same direction such that the conductors of one PCB are spaced from the conductors of an adjacent PCB by an insulating substrate. For example, the surface 68 on which the conductors are mounted faces upward on the PCBs in the first set 20, as illustrated in FIGS. 12 and 13. In one embodiment, an additional sheet of insulative material 62 may be positioned adjacent the surface 68 of one or more of the PCBs to reduce the flow of liquid/vapor across the surface.

At S104, the sets 20, 22 are positioned in a test cell container 13.

At S106, a predetermined quantity of a lubricant composition 16 to be tested is introduced to the container 13 to cover the first set 20 of PCBs.

At S108, an upper end of the test cell container 13 is closed with a removable closure 14, through which temperature probes 28, 30 are connected to a temperature monitor 32 and wires 72, 76 from each PCB are connected to the power source 40 and sensor component 42, respectively.

At S110, the test cell is inserted into the oven 26, where it is heated to the desired test temperature, such as at least 100° C., or at least 150° C., or at least 200° C. The temperatures of the liquid and vapor are monitored throughout the test. One of a set of different heating profiles may be evaluated. In one embodiment, once the test liquid has reached the desired test temperature, it is maintained at that temperature throughout the test by applying the heater when the temperature falls below a predetermined threshold temperature. Overheating may be controlled by switching off the heater and/or allowing cooler air into the chamber 24.

At S112, throughout a test, sensor signals are recorded by the sensor devices for each of the PCBs 21, which may include measuring a change in a magnetic field generated by the neutral conductors with magnetic field based sensors. Corresponding sensor measurements 46 are periodically output by the sensor component 42 to the data acquisition component 44, which stores the sensor measurements 46 in memory. In an exemplary non-invasive method, external sensors 96, 98, 100 are used to calculate the average resistance for each energized PCB 21, at each of a sequence of times, as illustrated in FIGS. 5 and 6.

At S114, the data processing component 48 retrieves the stored measurements 46 and generates deposition-information 50 based thereon.

The output information 50 may include one or more of:
a) an estimate of the amount of deposition on each PCB, e.g., as an inverse function of the resistance across the PCB, summed over a given time period,
b) an estimated rate of deposition on the PCB,
c) an estimated time to failure of the PCB, e.g., when the resistance of the PCB drops to a predetermined value,
d) a rating for the PCB, such as a pass/fail or a score, e.g., based on one or more of a)-c),
e) a comparison between PCBs, e.g., a ratio or a difference between PCBs in the same or different tests, for one or more of a)-d), and
combinations thereof, and
information derived therefrom.

In generating the output information 50, data for two or more PCBs may be aggregated (e.g., averaged) in generating the output information.

At S116, the information 50, or information generated based thereon, may be output to an output device.

At S118, at the completion of the test, an evaluation may be made of the PCB and/or of the lubricant composition using test methods, such as used oil analysis (ICP), microscopy and elemental analysis of the deposited material, e.g., via energy dispersive X-ray analysis (EDAX), spectroscopy, visual observations, and the like. These may be compared with pre-test analyses to determine differences.

The method ends at S120.

Examples of the ways in which the method can be used include:
a) Evaluation of different additives or additive packages for use in electrified devices, such as full electric transmissions and other devices,
b) Evaluation of different conductor materials for use in electrified and full electric transmissions and other devices with specific lubricant compositions,
c) Quality control: a rating may be given to a lubricant composition, without needing to know its composition.
d) Development of new lubricant compositions.

In one exemplary embodiment, the method is used to screen lubricant compositions for use in an electrified device, such as a motor or transmission system of an electric or hybrid gasoline/electric vehicle, where the conductors become exposed in the event of breakdown of a coating or sheathing for the electrical conductors, or where uncoated conductors are exposed to the vapor phase of the lubricant composition. In the event that conductive deposits form in such a device, damage to the electrical device can occur rapidly. Lubricant compositions that perform well in the test (little or no change in resistance of the PCB over time) can be selected as candidates for use in the electrified device, optionally after further reformulation and testing. The PCBs can be constructed to simulate the materials and geometries of the conductors used in the particular electrical device and the voltage provided by the power source and oven temperature selected to simulate those of the electrical device during operation. The lubricant compositions can be assessed using materials and geometries of conductors that are likely to be exposed to the liquid phase of the lubricant composition and materials and geometries of conductors that are likely to be exposed to the vapor phase of the lubricant composition.

In one embodiment, evaluated lubricant compositions are marketed with a rating as generated under specific test conditions of the exemplary test method.

In one embodiment, a predesigned additive package is tailored to meet a threshold rating under specific test conditions of the exemplary test method. For example, modifications are made to a previously designed additive package and each of the modifications is tested in a lubricant composition to identify at least one modification which meets the threshold rating and satisfies any other preselected properties of the lubricant composition.

EXAMPLE

Figure 15:
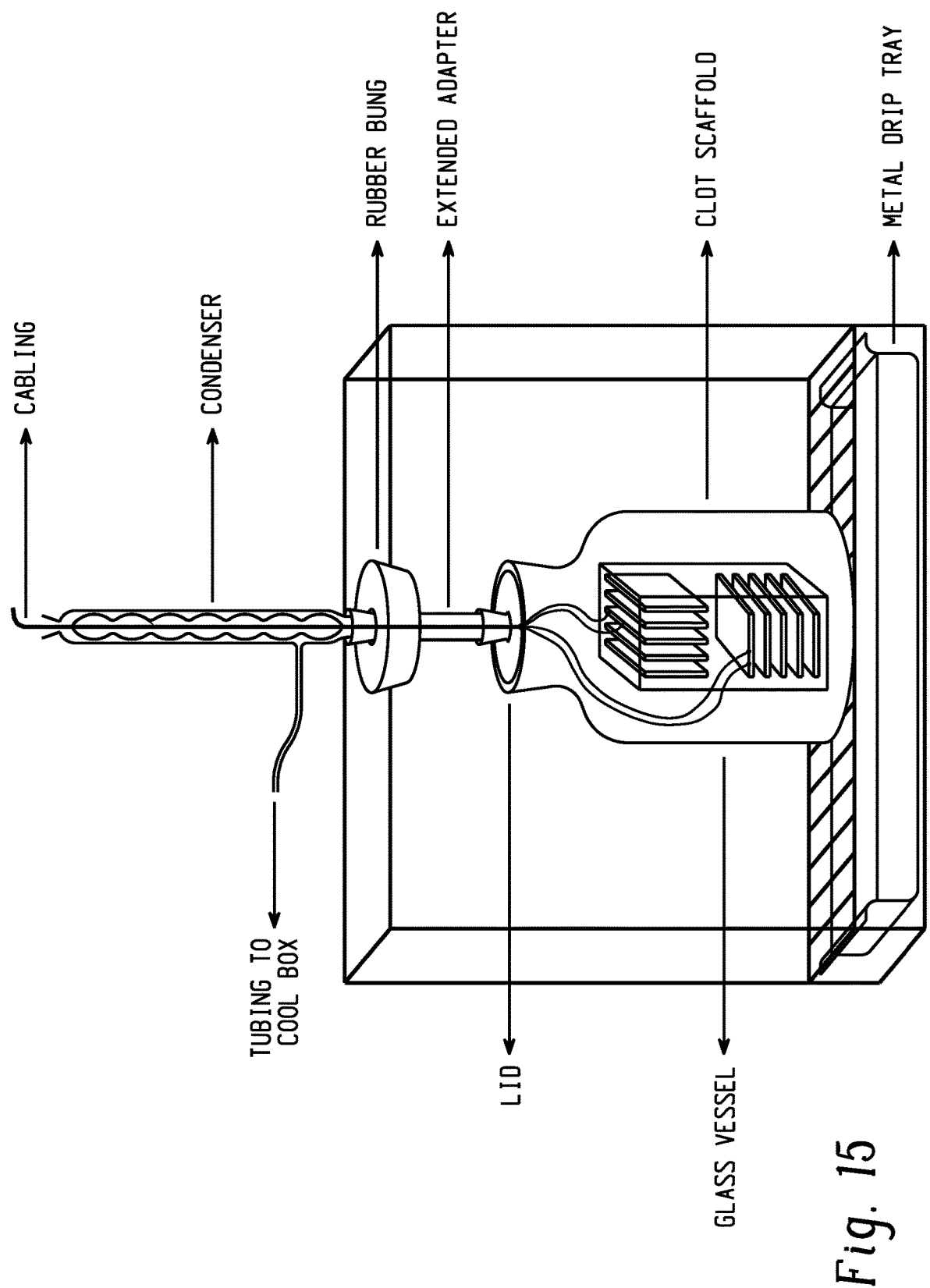
FIGS. 15 and 16 illustrate prototype test systems.
Figure 16:
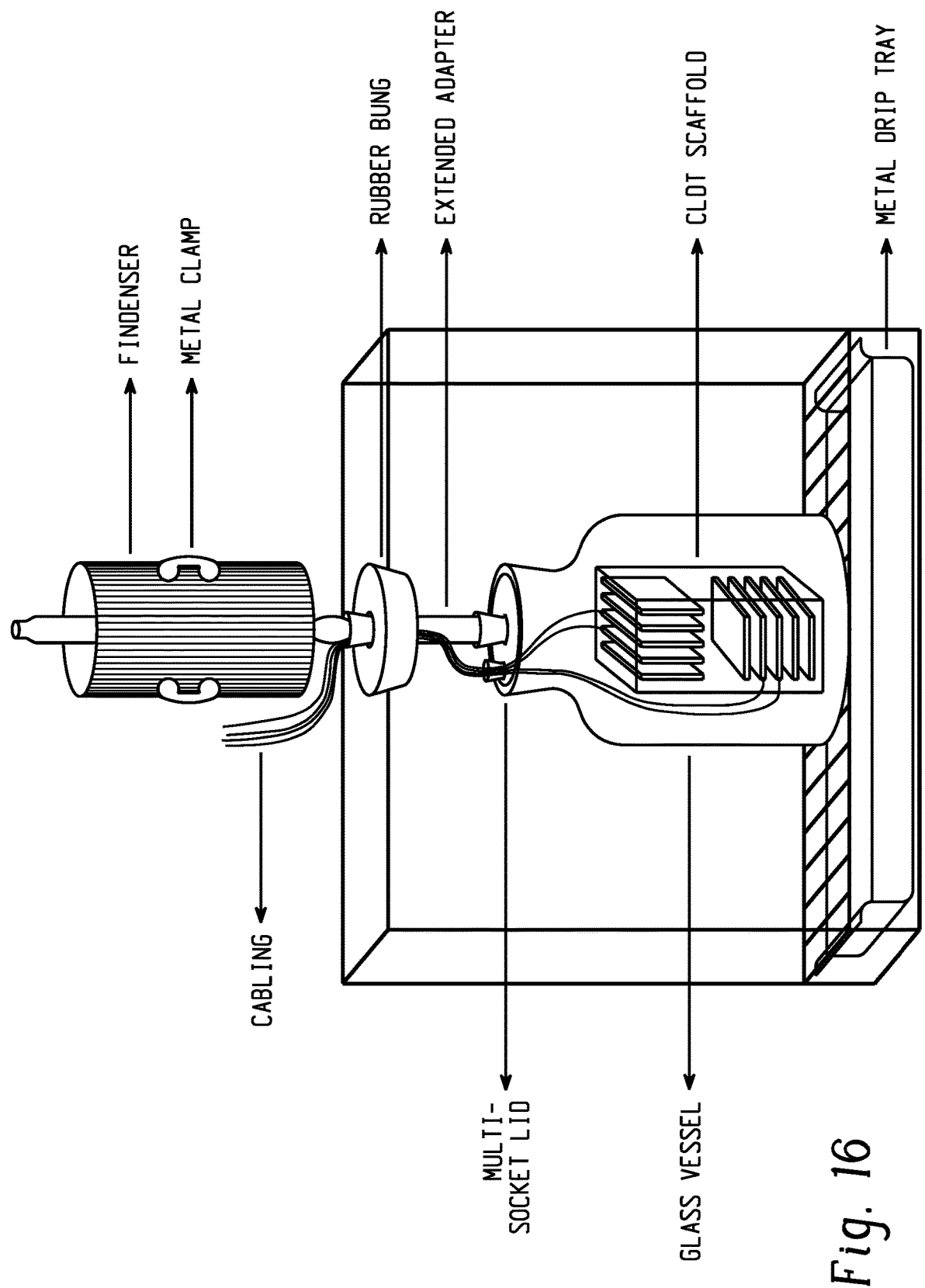

Ten printed circuit boards (PCB) containing a metal of interest (for example, copper, aluminum, gold, nickel or any combination) are arranged into two separate stacked layers, five in the solution of oil and five in the vapor space. Each stack contains up to five energized circuits with the ability to measure and record resistance measurements in real-time at temperatures up to 250° C. The formation of conducting layers results in detection of energy flow outside of the intended path. This is detected via the induced magnetic field caused by the flow of current. The fluid tested is contained within a closed, vented vessel, as illustrated in the prototype cell shown in FIG. 15. Temperature is measured in both the solution and vapor space via two Platinum Resistance Thermometers (PRTs). Vapor retention is controlled using a condenser (or Findenser, as illustrated in FIG. 16). During the test, data is acquired by the data acquisition component and processed by the data processing component. Analysis at the end of the test includes resistance measurements, used oil analysis (ICP), microscopy and elemental analysis of the deposited material, e.g., via energy dispersive X-ray analysis (EDAX).

Two lubricant compositions are tested to evaluate the system (denoted Lubricant A and Lubricant B). Conducting layer deposits are formed in Lubricant A in the vapor phase over the test period of 456 hours, however in the solution phase, this is not clearly apparent. Lubricant B does not form conducting layer deposits. Results are shown in TABLE 1, with values in bold indicating a measurable resistance value indicating the formation of a conducting layer deposit.

TABLE 1

| Vapor Phase | | |
| --- | --- | --- |
| Time (hrs) | Lubricant A (kΩ) | Lubricant B (kΩ) |
| 0 | >40000 | >40000 |
| 120 | 75.00 | >40000 |
| 144 | 95.00 | >40000 |
| 312 | 143.50 | >40000 |
| 336 | 172.40 | >40000 |
| 456 | 158.50 | >40000 |

A further four lubricants (C-F) are tested in the liquid and vapor phases. Results are as shown in TABLES 2 and 3.

TABLE 2

| Vapor Phase | | | | |
| --- | --- | --- | --- | --- |
| time (hrs) | Lubricant C (kΩ) | Lubricant D (kΩ) | Lubricant E (kΩ) | Lubricant F (kΩ) |
| 0 | >40000 | >40000 | >40000 | >40000 |
| 94 | 8600.00 | >40000 | 1.30 | >40000 |
| 144 | 16.00 | >40000 | 9.50 | >40000 |
| 321 | 19.00 | >40000 | 28.00 | >40000 |
| 336 | 20.00 | >40000 | 21.00 | >40000 |
| 456 | 16.00 | >40000 | 23.00 | >40000 |

TABLE 3

| Solution Phase | | | | |
| --- | --- | --- | --- | --- |
| time (hrs) | Lubricant C (kΩ) | Lubricant D (kΩ) | Lubricant E (kΩ) | Lubricant F (kΩ) |
| 0 | >40000 | >40000 | >40000 | >40000 |
| 94 | 7200.00 | 6800.00 | 5800.00 | 10600.00 |
| 144 | 6850.00 | 450.00 | 5300.00 | 10500.00 |
| 321 | 3390.00 | 46.00 | 690.00 | 10600.00 |
| 336 | 29.00 | 31.00 | 45.00 | 10500.00 |
| 456 | 29.00 | 8.20 | 27.00 | 10500.00 |

Each of the references mentioned herein is hereby incorporated by reference in its entirety.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed:

1. A system for detecting deposit formation on electrically-conductive materials in liquid and vapor phases, comprising the system, configured as a test system having the following:
    a test cell configured for receiving a test liquid that is a lubricant composition including a lubricating organic liquid as a major component;
    a heater, which heats the test liquid to generate a vapor phase of the test liquid in the test cell, and which is controlled by temperature sensors and a temperature control component to heat the liquid and vapor phases and maintain them at preselected, elevated temperature(s) during operation;
    a support frame, which supports at least a first set of electrical conductors configured for exposure to a liquid phase of the test liquid, when the test liquid is received in the test cell, and at least a second set of electrical conductors configured for exposure to the vapor phase of the test liquid, when the vapor phase is generated in the test cell, each of the first and second sets of electrical conductors including a live electrical conductor and a neutral electrical conductor;
    a power source, which supplies an electric current to each of the live electrical connectors;
    a sensor component, which detects an electrical property of each of the sets of electrical conductors, the electrical property changing in response to formation of an electrically-conductive deposit that connects the first and second electrical conductors in a respective set of electrical conductors, the sensor component including a sensor device for each of the sets of electrical conductors, and the sensor devices being located outside the test cell.

2. The system of claim 1, wherein the first and second sets of electrical connectors in each set are supported by a substrate.

3. The system of claim 2, wherein the first and second sets of electrical connectors in each set are interdigitated on the substrate.

4. The system of claim 2, wherein the first and second sets of electrical connectors in each set are spaced by a minimum gap, and the preselected, elevated temperature(s) is (are) at least about 100° C.

5. The system of claim 1, wherein the changing in the electrical property is a drop in electrical resistance.

6. The system of claim 1, wherein the sensor devices include magnetic field based sensors.

7. The system of claim 6, wherein the magnetic field based sensors detect a magnetic field generated when an electric current passes through the neutral electrical conductor.

8. The system of claim 1, wherein each set of electrical conductors is integrated into a respective printed circuit board.

9. The system of claim 8, wherein the support frame is configured for supporting a plurality of the respective printed circuit boards configured for. exposure to the liquid phase of the test liquid, and a different plurality of the respective printed circuit boards configured for exposure to the vapor phase of the test liquid.

10. The system of claim 1, further including a data acquisition component, which acquires sensor measurements from the sensor component; and a data processing component, which processes the acquired sensor measurements to generate output information.

11. The system of claim 10, wherein the output information includes at least one of the following (a-g):
    (a) an estimate of an amount of deposition for each set of electrical conductors, or for a printed circuit board incorporating the respective set;
    (c) an estimated rate of deposition for each set of electrical conductors, or for a printed circuit board incorporating the respective set;
    (d) an estimated time to failure for each set of electrical conductors, or for a printed circuit board incorporating the respective set;
    (e) a rating for each set of electrical conductors, or for a printed circuit board incorporating the respective set;
    (f) a comparison between first and second test liquids used in respective tests; and
    (g) combinations thereof, and/or information derived therefrom.

12. A method for detecting deposit formation on electrically-conductive materials in liquid and vapor phases of a test fluid, comprising the following steps, which are not necessarily conducted in series:
    providing a test cell for receiving the test fluid that is a lubricant composition including a lubricating organic liquid as a major component;
    supporting electrical conductors on a support frame, and placing the support frame with its supported electrical conductors in the test cell and introducing the test fluid into the test cell to immerse at least a first set of the electrical conductors in a liquid phase of the test fluid and at least a second set of the electrical conductors in a vapor phase of the test fluid, each of the first and second sets of electrical conductors including a live electrical conductor and a neutral electrical conductor;
    providing a heater that is configured to controllably heat the test fluid and maintain it at preselected, elevated temperature(s), and to generate the vapor phase of the test fluid in the test cell; and operating the heater;
    supplying an electric current to the live electrical conductors; and
    with a sensor component including a sensor device for each of the sets of electrical conductors and the sensor devices being located outside the test cell, detecting an electrical property of each of the sets of electrical conductors, the electrical property changing in response to formation of an elecrically-conductive deposit that connects the first and second electrical conductors in a respective set of, electrical conductors,
    wherein the method is carried out as a test method.

13. The method of claim 12, wherein the first and second electrical conductors in each set are supported on the same substrate.

14. The method of claim 12, wherein the changing in the electrical property is a drop in electrical resistance.

15. The method of claim 12, wherein the detecting of the electrical property of each of the sets of electrical conductors includes measuring a change in a magnetic field generated by the neutral conductors with magnetic field based sensors.

16. The method of claim 12, wherein the at least a first set of electrical conductors includes a plurality of first sets of electrical conductors, and the at least a second set of electrical conductors includes a plurality of second sets of electrical conductors; and the method includes supporting the plurality of first sets of electrical conductors and the plurality of second sets of electrical conductors on the same support frame.

17. The method of claim 12, wherein the lubricating organic liquid is an oil of lubricating viscosity; and the lubricant composition includes as a minor component at least one additive selected from the group consisting of antioxidant(s), detergent(s), dispersant(s), antiwear additive(s), corrosion inhibitor(s), viscosity modifier(s), metal passivator(s), pour point depressant(s), seal compatibility agent(s), antifoam agent(s), extreme pressure agent(s), friction modifier(s), and mixture(s) thereof.

18. The method of claim 12, wherein the lubricating organic liquid is an oil, and the preselected, elevated temperature(s) is (are) at least about 100° C.

19. In combination, the system of claim 1 and a collection of printed circuit boards, wherein:
    the support frame includes a lower portion, which supports a first set of the printed circuit boards, and an upper portion, which supports a second set of the printed circuit boards above the first set of printed circuit boards, the upper portion being supported on the lower portion; and
    each of the printed circuit boards includes a live electrical conductor and a neutral electrical conductor, spaced by the live electrical conductor by a minimum 1 gap, which maintains an electrical resistance between the live electrical conductor and the neutral electrical conductor until the gap is bridged by an electrically conducting deposit.

20. The combination of claim 19, wherein at least one of the lower portion and the upper portion includes a biasing member, which applies a force to the respective set of printed circuit boards.

21. A test cell comprising the following:
a collection of printed circuit boards, with a support frame having a lower portion supporting a first set of said boards, and an upper portion supporting a second set of said boards above the first set of said boards, the upper portion supported on the lower portion, with each of said boards having a live and a neutral electrical conductor, spaced by a minimum gap, which maintains an electrical resistance between the live and neutral electrical conductors until the gap is bridged by an electrically conducting deposit during testing with the test cell; and
a container configured for holding said collection, and a liquid phase and a vapor phase of a test fluid, such that, during the testing with the test cell:
the live electrical conductor and the neutral electrical conductor of each of the first set of said boards are immersed in the liquid phase of the test fluid; and
the live electrical conductor and the neutral electrical conductor of each of the second set of said boards are immersed in the vapor phase of the test fluid,
wherein the test cell is configured to be used in a system for detecting deposit formation on electrically-conductive materials in the liquid and vapor phases of the test fluid, and the system is configured such that it can be employed as a test system.

* * * * *